(12) United States Patent
Intrator

(10) Patent No.: US 12,076,570 B2
(45) Date of Patent: *Sep. 3, 2024

(54) SYSTEMS AND METHODS FOR COOPERATIVE INVASIVE AND NONINVASIVE BRAIN STIMULATION

(71) Applicant: NeuroSteer Inc., New York, NY (US)

(72) Inventor: Nathan Intrator, Herzliya (IL)

(73) Assignee: NEUROSTEER INC., New York, NY (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/816,536

(22) Filed: Aug. 1, 2022

(65) Prior Publication Data
US 2023/0106160 A1    Apr. 6, 2023

Related U.S. Application Data

(63) Continuation of application No. 17/067,390, filed on Oct. 9, 2020, now Pat. No. 11,400,300, which is a
(Continued)

(51) Int. Cl.
*A61N 1/36* (2006.01)
*A61B 5/00* (2006.01)
(Continued)

(52) U.S. Cl.
CPC ............ *A61N 1/3727* (2013.01); *A61B 5/316* (2021.01); *A61B 5/4836* (2013.01); *A61B 5/7282* (2013.01); *A61N 1/0534* (2013.01); *A61B 5/0006* (2013.01); *A61B 5/2415* (2021.01); *A61B 5/4848* (2013.01); *A61N 1/36067* (2013.01); *A61N 1/36075* (2013.01); *A61N 1/36078* (2013.01); *A61N 1/36092* (2013.01); *A61N 1/36096* (2013.01)

(58) Field of Classification Search
CPC ............ A61N 1/36096; A61N 1/37067; A61N 1/36078; A61B 5/4836
See application file for complete search history.

(56) References Cited

U.S. PATENT DOCUMENTS 7,856,264 B2    12/2010    Firlik et al.
10,799,708 B2   10/2020    Intrator
(Continued)

FOREIGN PATENT DOCUMENTS

WO    2018026710 A1    2/2018

*Primary Examiner* — William J Levicky
(74) *Attorney, Agent, or Firm* — Greenberg Traurig, LLP

(57) ABSTRACT

Methods and systems for optimizing invasive and noninvasive brain stimulation are described herein. In a particular embodiment, methods and systems for a combinatorial, iterative approach to modify behavior are presented wherein deep brain stimulation (DBS) and other brain stimulation therapies are implemented in combination with monitoring the brain activity of an individual to optimize the effectiveness of the combinatorial approach to modify behavior. Methods described herein are iterative and systems described herein are utilized in iterative fashion. In a particular embodiment, modifying behavior provides a therapy for an individual in need thereof.

20 Claims, 7 Drawing Sheets
(7 of 7 Drawing Sheet(s) Filed in Color)

Related U.S. Application Data continuation of application No. 16/575,127, filed on Sep. 18, 2019, now Pat. No. 10,799,708.

(60) Provisional application No. 62/732,905, filed on Sep. 18, 2018.

(51) Int. Cl.
*A61B 5/316* (2021.01)
*A61N 1/05* (2006.01)
*A61N 1/372* (2006.01)
*A61B 5/24* (2021.01)

(56) References Cited

U.S. PATENT DOCUMENTS

| | | |
|---|---|---|
| 2002/0182574 A1 | 12/2002 | Freer et al. |
| 2011/0270074 A1 | 11/2011 | deCharms |
| 2013/0245424 A1 | 9/2013 | deCharms |
| 2014/0223462 A1* | 8/2014 | Aimone .......... A61B 5/369 725/10 |
| 2017/0347906 A1 | 12/2017 | Intrator |

* cited by examiner

SYSTEMS AND METHODS FOR COOPERATIVE INVASIVE AND NONINVASIVE BRAIN STIMULATION

RELATED APPLICATIONS

This application is a continuation of U.S. patent application Ser. No. 17/067,390, filed Oct. 9, 2020, which is a continuation of U.S. patent application Ser. No. 16/575,127, now U.S. Pat. No. 10,799,708, filed Sep. 18, 2019, which claims priority of U.S. Provisional Application No. 62/732,905, filed Sep. 18, 2018, the entirety of which are incorporated herein by reference for all purposes.

FIELD OF THE INVENTION

The present invention relates to a method and system for optimizing invasive and noninvasive brain stimulation. More particularly, a method and system for a combination therapy wherein deep brain stimulation (DBS) and other brain stimulation therapies are implemented in combination with monitoring the brain activity of an individual using methods and systems described herein to optimize efficacy of the combination therapy. In particular, the present invention relates to a system for monitoring an individual's brain activity responsive to DBS, and other physiological parameters, and environmental parameters, correlating the monitored brain activity with the DBS and physiological and environmental parameters, and from the correlation, determining if the DBS should be altered to improve efficacy of the DBS.

BACKGROUND OF THE INVENTION

Electroencephalography (EEG) is one method to monitor electrical activity of the brain. It is typically noninvasive, with the electrodes placed along the scalp, however, invasive electrodes may be used in specific applications. EEG measures voltage fluctuations resulting from ionic current within the neurons of the brain. However, the sensitivity of the EEG electrodes limits detection to small regions of the brain, close to each electrode, thus limiting the spatial resolution of EEG.

SUMMARY OF THE INVENTION

In an aspect, a method is presented comprising:
detecting:
  i. a particular activity performed by an individual and
  ii. brain electrical activity of the individual associated with the particular activity;
administering at least one stimulus to modulate brain electrical activity of an individual while the individual is performing the particular activity; and
detecting changes in the brain electrical activity of the individual responsive to the at least one stimulus, wherein the at least one stimuli provides a specific stimulation pattern to promote the ability of the individual to perform the particular activity;
continuously detecting brain electrical activity of the individual while the individual is performing the particular activity;
continuously projecting, in real time, the detected brain electrical activity of the individual while the individual is performing the particular activity onto a denoised optimal set of wavelet packet atoms to obtain a particular set of projections of the individual, wherein the denoised optimal set of wavelet packet atoms is based on brain electrical activity collected from a plurality of individuals performing the particular activity,
wherein each of the plurality of individuals performing the particular activity exhibits a pre-determined level of ability with respect to the particular activity and wherein the brain electrical activity collected from the plurality of individuals is representative brain electrical activity of the plurality of individuals performing the particular activity at the predetermined level of ability;
continuously assessing, in real time, the brain electrical activity of the individual while the individual is performing the particular activity relative to the representative brain electrical activity of the plurality of individuals performing the particular activity by applying at least one machine learning algorithm to the particular set of projections of the individual,
  wherein the at least one machine learning algorithm is trained by the plurality of individuals performing the particular activity and the brain electrical activity collected from the plurality of individuals associated with performing the particular activity;
continuously determining a relationship between:
  i. the particular activity performed by the individual,
  ii. the brain electrical activity of the individual associated with the particular activity,
  iii. the continuously assessing, in real time, of the brain electrical activity of the individual associated with the particular activity relative to the representative brain electrical activity of the plurality of individuals performing the particular activity, and
  iv. the at least one stimuli; and
continuously adjusting, based on the relationship, the specific stimulation pattern to promote the ability of the individual to perform the activity.

In an embodiment of the method, the administering the at least one stimulus is performed by at least one apparatus. In an embodiment of the method, the at least one apparatus is an invasive deep brain stimulation device or a non-invasive brain stimulator.

In an embodiment of the method, the invasive deep brain stimulation device comprises at least one of an electrode or electrodes, a chemical distributing device, a magnetic producing electrode or a light producing electrode; and the non-invasive brain stimulator comprises at least one of a stimulator of one or more of the senses, a drug delivery device, or a magnetic source, a vibro-acoustic source, an ultrasound source, or an electrical source providing stimulation at a certain location or locations on the skull or near other nerves in the body.

In an embodiment of the method, the method further comprises collecting other environmental and physiological data from the individual while the individual is performing the particular activity.

In an embodiment of the method, promoting the ability of the individual to perform the activity comprises enhancing the ability of the individual to perform the activity to at least partially achieve that of the pre-determined level of ability with respect to the particular activity. In an embodiment of the method, promoting the ability of the individual to perform the activity also promotes the ability of the individual to perform at least one additional activity.

In an embodiment of the method, the individual has a disease or disorder that impairs the individual's ability to perform the particular activity. In an embodiment of the method, the disease or disorder comprises at least one of Parkinson's disease, tremors, motor dysfunction, dyskinesia, gate freeze, epilepsy, migraine headaches, pain, anxiety, depression, mood swings, attention deficit disorders, sleep disorders, or cognitive decline disorders.

In an embodiment of the method, the individual has Parkinson's disease; and the particular activity is walking; and the continuously adjusting, based on the relationship, the specific stimulation pattern promotes the ability of the individual having Parkinson's disease to walk.

In an embodiment of the method, the individual has gate freeze, and the specific stimulation pattern promotes the ability of the individual to resume walking.

In an embodiment of the method, the individual has a sleep disorder; and the particular activity is sleeping; and the continuously adjusting, based on the relationship, the specific stimulation pattern promotes the ability of the individual having the sleep disorder to sleep.

In an embodiment of the method, the individual has a cognitive disorder; and the particular activity is a cognitive challenge; and the continuously adjusting, based on the relationship, the specific stimulation pattern promotes the ability of the individual with the cognitive disorder to meet the cognitive challenge.

In an embodiment of the method, the individual has an anxiety disorder; and the particular activity is an anxiety provoking activity; and the continuously adjusting, based on the relationship, the specific stimulation pattern promotes the ability of the individual to perform the anxiety provoking activity by reducing stress levels of the individual with the anxiety disorder responsive to the anxiety provoking activity.

In an aspect, a method is presented comprising:
detecting:
  i. a particular activity performed by an individual, wherein the individual has a disease or disorder that impairs the individual's ability to perform the particular activity; and
  ii. brain electrical activity of the individual associated with the particular activity;
administering at least one stimulus to modulate brain electrical activity of an individual while the individual is performing the particular activity; and
detecting changes in the brain electrical activity of the individual responsive to the at least one stimulus, wherein the at least one stimuli provides a specific stimulation pattern to promote the ability of the individual to perform the particular activity;
continuously detecting brain electrical activity of the individual while the individual is performing the particular activity;
continuously projecting, in real time, the detected brain electrical activity of the individual while the individual is performing the particular activity onto a denoised optimal set of wavelet packet atoms to obtain a particular set of projections of the individual, wherein the denoised optimal set of wavelet packet atoms is based on brain electrical activity collected from a plurality of individuals performing the particular activity,
wherein each of the plurality of individuals performing the particular activity is an individual exhibiting a pre-determined level of ability with respect to the particular activity and wherein the brain electrical activity collected from the plurality of individuals is representative brain electrical activity of the plurality of individuals performing the particular activity at a pre-determined level of ability;
continuously assessing, in real time, the brain electrical activity of the individual while the individual is performing the particular activity relative to the representative brain electrical activity of the plurality of individuals performing the particular activity by applying at least one machine learning algorithm to the particular set of projections of the individual,
  wherein the at least one machine learning algorithm is trained by the plurality of individuals performing the particular activity and the brain electrical activity collected from the plurality of individuals associated with performing the particular activity;
continuously determining a relationship between:
  i. the particular activity performed by the individual,
  ii. the brain electrical activity of the individual associated with the particular activity,
  iii. the continuously assessing, in real time, of the brain electrical activity of the individual associated with the particular activity relative to the representative brain electrical activity of the plurality of individuals performing the particular activity, and
  iv. the at least one stimulus; and
continuously adjusting, based on the relationship, the specific stimulation pattern to promote the ability of the individual to perform the activity, thereby reducing at least one symptom of the disease or disorder.

In an embodiment of the method, impairment of an individual's ability to perform the particular activity is a symptom characteristic of the disease or disorder.

In an embodiment of the method, the administering the at least one stimuli is performed by at least one apparatus. In an embodiment of the method, the at least one apparatus is an invasive deep brain stimulation device or a non-invasive brain stimulator. In an embodiment of the method, the invasive deep brain stimulation device comprises at least one of an electrode or electrodes, a chemical distributing device, a magnetic producing electrode or a light producing electrode; and the non-invasive brain stimulator comprises at least one of a stimulator of one or more of the senses, a drug delivery device, or a magnetic source, a vibro-acoustic source, an ultrasound source, or an electrical source providing stimulation at a certain location or locations on the skull or near other nerves in the body.

In an embodiment of the method, the method further comprises collecting other environmental and physiological data from the individual while the individual is performing the particular activity.

In an embodiment of the method, promoting the ability of the individual to perform the activity comprises enhancing the ability of the individual to perform the activity to at least partially achieve that of the pre-determined level of ability with respect to the particular activity. In an embodiment of the method, promoting the ability of the individual to perform the activity also promotes the ability of the individual to perform at least one additional activity.

In an embodiment of the method, the disease or disorder comprises at least one of Parkinson's disease, tremors, motor dysfunction, dyskinesia, gate freeze, epilepsy, migraine headaches, pain, anxiety, depression, mood swings, attention deficit disorders, sleep disorders, or cognitive decline disorders.

In an embodiment of the method, the disease is Parkinson's disease; and the particular activity is walking; and the continuously adjusting, based on the relationship, the specific stimulation pattern promotes the ability of the individual having Parkinson's disease to walk.

In an embodiment of the method, the individual has gate freeze, and the specific stimulation pattern promotes the ability of the individual to resume walking.

In an embodiment of the method, the disorder is a sleep disorder; and the particular activity is sleeping; and the continuously adjusting, based on the relationship, the specific stimulation pattern promotes the ability of the individual having a sleep disorder to sleep.

In an embodiment of the method, the disorder is a cognitive disorder; and the particular activity is a cognitive challenge; and the continuously adjusting, based on the relationship, the specific stimulation pattern promotes the ability of the individual with the cognitive disorder to meet the cognitive challenge.

In an embodiment of the method, the individual has an anxiety disorder; and the particular activity is an anxiety provoking activity; and the continuously adjusting, based on the relationship, the specific stimulation pattern promotes the ability of the individual to perform the anxiety provoking activity by reducing stress levels of the individual with the anxiety disorder responsive to the anxiety provoking activity.

In an embodiment of the method, the individual has dyskinesia; and the particular activity is sustained motionlessness; and the continuously adjusting, based on the relationship, the specific stimulation pattern reduces movement characteristic of dyskinesia.

In an aspect, a system is presented comprising:
an apparatus configured to be worn on an individual's head to detect:
  i. a particular activity performed by the individual;
  ii. brain electrical activity of the individual associated with the particular activity,
    wherein the brain electrical activity of the individual is detected continuously while the individual is performing the particular activity; and
  iii. at least one stimulus configured to modulate brain electrical activity of the individual while the individual is performing the particular activity,
    wherein the at least one stimuli provides a specific stimulation pattern to promote the ability of the individual to perform the activity, and
    wherein detecting changes in the brain electrical activity of the individual responsive to the at least one stimulus is indicative of effectiveness of the at least one stimuli to promote the ability of the individual to perform the activity; and
a specifically programmed computer system,
  wherein the specifically programmed computer system comprises:
    i. a non-transient memory, electronically storing particular computer executable program code; and
    ii. at least one computer processor which, when executing the particular program code, becomes a specifically programmed computer processor configured to perform at least the following operations:
      continuously projecting, in real time, the detected brain electrical activity of the individual while the individual is performing the particular activity onto a denoised optimal set of wavelet packet atoms to obtain a particular set of projections of the individual, wherein the denoised optimal set of wavelet packet atoms is based on brain electrical activity collected from a plurality of individuals performing the particular activity,
        wherein each of the plurality of individuals performing the particular activity exhibits a pre-determined level of ability with respect to the particular activity and wherein the brain electrical activity collected from the plurality of individuals is representative brain electrical activity of the plurality of individuals performing the particular activity at a pre-determined level of ability;
      continuously assessing, in real time, the brain electrical activity of the individual while the individual is performing the particular activity relative to the representative brain electrical activity of the plurality of individuals performing the particular activity by applying at least one machine learning algorithm to the particular set of projections of the individual,
        wherein the at least one machine learning algorithm is trained by the plurality of individuals performing the particular activity and the brain electrical activity collected from the plurality of individuals associated with performing the particular activity;
      continuously determining a relationship between:
        i. the particular activity performed by the individual,
        ii. the brain electrical activity of the individual associated with the particular activity,
        iii. the continuously assessing, in real time, of the brain electrical activity of the individual associated with the particular activity relative to the representative brain electrical activity of the plurality of individuals performing the particular activity, and
        iv. the at least one stimulus; and
      continuously adjusting, based on the relationship, the specific stimulation pattern to promote the ability of the individual to perform the activity.

In an embodiment of the system, the system further comprises at least one apparatus configured to administer the at least one stimulus. In an embodiment of the system, the at least one apparatus is an invasive deep brain stimulation device or a non-invasive brain stimulator. In an embodiment of the system, the invasive deep brain stimulation device comprises at least one of an electrode or electrodes, a chemical distributing device, a magnetic producing electrode or a light producing electrode; and the non-invasive brain stimulator comprises at least one of a stimulator of one or more of the senses, a drug delivery device, or a magnetic source, a vibro-acoustic source, an ultrasound source, or an electrical source providing stimulation at a certain location or locations on the skull or near other nerves in the body. In an embodiment of the system, the system further comprises at least one apparatus configured to collect other environmental and physiological data from the individual while the individual is performing the particular activity.

In an embodiment of the system, promoting the ability of the individual to perform the activity comprises enhancing the ability of the individual to perform the activity to at least partially achieve that of the pre-determined level of ability with respect to the particular activity. In an embodiment of the system, promoting the ability of the individual to perform the activity also promotes the ability of the individual to perform at least one additional activity.

In an embodiment of the system, the individual has a disease or disorder that impairs the individual's ability to perform the particular activity. In an embodiment of the system, the disease or disorder comprises at least one of Parkinson's disease, tremors, motor dysfunction, dyskinesia, gate freeze, epilepsy, migraine headaches, pain, anxiety, depression, mood swings, attention deficit disorders, sleep disorders, or cognitive decline disorders.

In an embodiment of the system, the individual has Parkinson's disease; and the particular activity is walking;

and the continuously adjusting, based on the relationship, the specific stimulation pattern promotes the ability of the individual having Parkinson's disease to walk.

In an embodiment of the system, the individual has gate freeze, and the specific stimulation pattern promotes the ability of the individual to resume walking.

In an embodiment of the system, the individual has a sleep disorder; and the particular activity is sleeping; and the continuously adjusting, based on the relationship, the specific stimulation pattern promotes the ability of the individual having a sleep disorder to sleep.

In an embodiment of the system, the individual has an anxiety disorder; and the particular activity is an anxiety provoking activity; and the continuously adjusting, based on the relationship, the specific stimulation pattern promotes the ability of the individual to perform the anxiety provoking activity by reducing stress levels of the individual with the anxiety disorder responsive to the anxiety provoking activity.

In an embodiment of the system, the individual has dyskinesia; and the particular activity is sustained motionlessness; and the continuously adjusting, based on the relationship, the specific stimulation pattern reduces movement characteristic of dyskinesia.

In an embodiment of the system, the specifically programmed computer processor is further configured to determine the denoised optimal set of wavelet packet atoms based on: obtaining from the plurality of individuals at least 100 recordings of electrical signal data representative of general brain activity of the plurality of individuals performing the specific task; obtaining an optimal set of wavelet packet atoms from the detected brain electrical activity of the plurality of individuals performing the specific task, by:

1. selecting a mother wavelet selected from the group consisting of: Haar, Coiflet Daubehies, and Meyer wavelet families;
2. determining, by the specifically programmed processor, an optimal set of wavelet packet atoms, by:
   a. causing the detected brain electrical activity of the plurality of individuals performing the specific task to be deconstructed into a plurality of wavelet packet atoms, using the selected mother wavelet;
   b. storing the plurality of wavelet packet atoms in at least one first computer data object;
   c. determining the optimal set of wavelet packet atoms using the selected mother wavelet, and storing the optimal set of wavelet packet atoms in at least one second computer data object, wherein the determining is via utilizing a Coifman-Wickerhauser Best Basis algorithm;
   d. denoising the obtained optimal set of wavelet packet atoms from the detected brain electrical activity of the plurality of individuals performing the specific task to obtain the denoised optimal set of wavelet packet atoms;
   e. reordering, the denoised optimal set of wavelet packet atoms from the detected brain electrical activity of the plurality of individuals performing the specific task, to obtain the pre-determined ordering of the denoised optimal set of wavelet packet atoms from the detected brain electrical activity of the plurality of the individuals performing the specific task, by determining a minimum path, by:
3. projecting the detected brain electrical activity of the plurality of individuals performing the specific task on to the denoised optimal set of wavelet packet atoms, to obtain a set of projections corresponding to a plurality of channels,
   wherein each respective projection is a result of a convolution of an electrical signal in each time window of the detected brain electrical activity and a wavelet packet atom;
4. determining a collection of wire lengths for every data point within the set of projections,
   wherein each wire length is determined by a correlation of every two projections;
5. storing the collection of wire lengths for the set of projections in at least one third computer data object;
6. iteratively, determining, by the specifically programmed processor, a plurality of (i) orders of projections, and (ii) respective wire lengths, by
   i. determining a respective wire length for every data point in each respective projection of the set of projections by determining either a mean or a sum of an absolute distance of a statistical measure of each respective projection of each particular channel from at least one other projection of at least one other channel which is adjacent to the particular channel; and
   ii. storing the wire length data in at least one fourth computer data object; and
7. determining, from the plurality of respective wire lengths, a particular order of projections that minimizes either the mean or sum of the plurality of respective wire lengths across the set of projections and across all individuals within the plurality of individuals performing the specific task so as to identify the pre-determined ordering of the denoised optimal set of wavelet packet atoms.

In an embodiment of the system, the visual indication comprises a visual map, generated by: calculating at least one of a standard deviation of a time window of each projection of the particular set of projections of the individual and an energy of each projection of the particular set of projections of the individual, and assigning a color to each projection of the particular set of projections of the individual, based on at least one of the standard deviation of the time window and the energy of each respective projection.

In an embodiment of the system, the apparatus comprises two electrodes configured to detect the brain electrical activity of the individual while the individual is performing the particular activity.

In all of the methods and systems described herein the plurality of individuals performing a specific task are chosen based on a feature in common among the plurality of individuals. Common features may comprise, for example: a certain score or score within a particular range of performance in a particular cognitive or other brain testing task, a particular genetic profile (e.g. all have (or do not have) a certain mutation), gender, and/or age.

Brain stimulation is used to treat a variety of brain disorders including, without limitation, brain injury, cognitive decline, Alzheimer's disease, Parkinson's disease, epilepsy, bulimia, depression, anxiety, cognitive enhancement, recovery from minimal consciousness, recovery from traumatic brain injury (TBI), recovery from anesthesia, and chronic pain. The stimulation itself frequently includes invasive techniques, such as, for example, under the skull and deep brain stimulation. Noninvasive techniques, such as, for example, electrical stimulation using alternating current (AC) and/or direct current (DC), magnetic stimulation, sound stimulation, ultrasound stimulation, optical stimulation, and oxygen based stimulation (e.g., treatment using a hyperbaric chamber) may also be used alone or in conjunction with invasive techniques. In order to maximize efficacy of such stimuli, a wide variety of parameters must be personalized and optimized for the specific disorder and the subject afflicted by the specific disorder. In particular, sensing the brain activity while stimulating can providing modifications to the stimulating parameters and can provide real-time indications whether the change in stimulation parameters has reach a desired effect on the brain activity, thus enabling a quick personalization of the stimulation and better indications on when the stimulation is needed and its effectiveness.

Such stimulation parameters include, without limitation: the location in or on the skull where the stimulation is provided, and the direction of the stimulatory beam; the energy or current and duration of the stimulation; the pattern of the stimulation (frequency or more complicated pattern); and/or the number of stimuli, the duration, and the duration of intervals between stimuli (intermittent, discontinuous stimulation).

In a particular embodiment, the stimulation is triggered by a certain event, such as the onset of pre-ictal activity. Such abnormal electrical activity can be detected as described in WO 2016/132228 and U.S. Patent Application Publication No. 2017/0347906, the entire content of each of which is incorporated herein by reference.

The current state of the art in the optimization of the stimulation includes a pre-set or a collection of pre-set stimulation parameters. Optimization is then performed by either manually changing the preset parameters while observing or questioning the subject about how he/she feels. Such protocols are known in the art and described in, for example, U.S. Pat. No. 8,295,935, the entire content of which is incorporated herein by reference. Observation may also be used to evaluate tremor severity and reduction thereof and/or degree of dyskinesia and reduction thereof. After the process of optimization with a neurologist or a stimulation expert is complete, the parameters are set based on the evaluation of the skilled practitioner.

In one embodiment the brain activity can be monitored continuously before and during the stimulation. The stimulation can be modified according to some schedule and the brain activity registered. Optimal stimulation parameters are then set based on achieving a desired brain activity.

In one embodiment, specific brain states such as fatigue, lack of attention, or poor cognitive functioning may be detected. In one embodiment, the brain state can be detected based on quantitative electroencephalography (qEEG) theory, such as determination of the increase in Delta energy, or reduction of Gamma at a certain brain region. Based on the determination of the specific condition, brain stimulation can be provided to activate the frontal lobe or to activate other areas based on protocols known in the art of brain stimulation. Methods and systems described herein improve the sensitivity of EEG sensing and specificity resulting from the multi-component decomposition of the EEG signal that is based on advanced time/frequency harmonic analysis.

In a particular embodiment, a method for optimizing DBS for Parkinson's patients is presented. In accordance with this embodiment, DBS may be optimized in real time based on brain activity. In a particular embodiment thereof, the intensity, positioning, frequency of the stimulation, and/or a general stimulation pattern may be adjusted based on brain activity.

As used herein, the term "specific stimulation pattern" is used to refer to at least one stimulus having a particular morphology of the signal, duration, spectral content, repetition rate (how many times it is provided and what is the time between stimuli), electrode location, strength of the stimulating signal (voltage or current) and all combinations thereof that is/are chosen based on the indication with respect to promoting the ability of an individual to perform a task (e.g., promoting the ability of a subject with Parkinson's disease or a dyskinesia to, e.g., walk or control involuntary movements).

As used herein, the phrase "to at least partially achieve that of the pre-determined level of ability with respect to the particular task" refers to enhancing the brain activity associated with the task and sometimes to enhance the ability of the individual to perform the task to at least 5%, 10%, 20%, 30%, 40%, 50%, 60%, 70%, 80%, 90%, or 100% of the level of an individual having a pre-determined level of ability, or a predetermined level of brain activity with respect to the particular task. Enhancing the ability of an individual may be determined via a variety of means, including, for example, subjective evaluation of the individual trying to enhance his/her ability to perform the task, visual assessment, gyroscopic assessment, or other criteria such as, e.g., determining the speed and/or accuracy with which an individual performs the task. Enhancing the brain activity of the individual is measured by means of measuring brain activity. In one embodiment, this can be seen in FIG. 5 where the effect of 10 minutes of tDCS on brain activity during a memory task is presented.

As used herein, a pre-determined level of ability refers to a particular level of ability to perform a particular activity for a plurality of individuals selected based on at least one common feature of the plurality of individuals. Such features may, for example, include physiological measurements based on a score in a determinative test or assessment pertaining to physical, intellectual (e.g., a high cognitive score as determined by a trained professional), or emotional attributes; age; gender; genetics; etc., such that the plurality of individuals is selected based on the at least one common feature.

In a particular embodiment, the plurality of individuals performing a similar task is selected chosen from those with a certain score of performance at a certain cognitive or other brain testing task, specific genetic group, e.g. all have (or do not have) a certain mutation, and gender and age match.

Deep Brain Stimulation (DBS) includes one or more electrodes that are inserted surgically into the brain. There are several ways to determine the exact location of the stimulator using functional magnetic resonance imaging (fMRI) or multiple electrode electroencephalography (EEG). Stimulators may, for example, include long electrodes with multiple transmission sites thereon. Inclusion of multiple transmission sites facilitates altering the specific transmission pattern, location, and orientation of stimulation after surgical implantation using an external remote control. Current practice comprises clinical evaluation of the patient after implantation by a trained practitioner (e.g., a neurologist), on which basis stimulation parameters are optimized. The practitioner may, for example, evaluate the patient based on observing the patient at rest or participating in some activity to determine, for example, the amount of tremor (e.g., severity and/or frequency) or general behavior, physical palpation of a body part affected by the disease/condition (e.g., feeling the rigidity of the limbs), and/or asking the patient how he/she feels.

A tool for enabling post-operation optimization of DBS parameters is highly desired. Indeed, general monitoring and observing DBS effect on brain activity is important for achieving optimal clinical efficacy. Prior to the present inventor's discovery of the benefits of combinatorial therapy, wherein DBS is used in conjunction with brain activity monitoring as described herein, a clinical practitioner would essentially have to optimize DBS treatment empirically by trial and error, using the patient as an experimental test subject. In accordance with combinatorial methods described herein, the parameters of DBS can be altered/modified using objective, rather subjective, indicators. As described herein, measuring brain activity in particular regions, for example, cognitive region A, as measured by detecting, for example, features from 20 to 60 offers an indicator of efficacy of DBS. See also Example 3 presented herein below. See also U.S. Pat. No. 9,955,905, the entire content of which is incorporated herein by reference.

In accordance with combinatorial methods described herein, the parameters of DBS can also be changed dynamically during brain activity, for example, in the case of DBS used for treating epilepsy, where electrodes sense abnormal activity and may be used to react and counter abnormal activity. Several embodiments of detection of pre-ictal or ictal activity are described in U.S. Pat. No. 9,955,905 and PCT Publication WO 2017/212333, the entire content of each of which is incorporated herein by reference. The specific embodiment describes a way to observe the effect of the DBS during specific motor and cognitive challenges, and provide an indication of determining the patterns which induce brain activity that is more desired, for example, closer to a brain activity of a healthy subject performing such tasks. Machine learning can be used to examine the brain activity patterns and determine automatically the more desired patterns. The described optimization method can be used for other aspects of DBS and said other types of stimulation.

As used herein, the term "healthy subject" refers to a subject who does not have a particular disease or disorder. Accordingly, a healthy subject performing a task would be able to perform a task at a pre-determined level of ability and would have corresponding brain activity characteristic or representative of a healthy subject performing the task at the pre-determined level of ability.

In an aspect, the present invention provides an exemplary inventive system that includes at least the following components: an apparatus configured to be worn on an individual's head, and record: i) the individual's brain electrical activity, ii) at least one physiological parameter of the individual, selected from the group consisting of: heart rate, blood oxygen levels, body temperature, respiration rate, skin temperature, skin conductivity, and movement, and iii) at least one environmental parameter; a specifically programmed computer system; where the specifically programmed computer system includes: i) a non-transient memory, electronically storing particular computer executable program code; and ii) at least one computer processor which, when executing the particular program code, becomes a specifically programmed computer processor configured to perform at least the following operations: continuously obtaining a recording of electrical signal data representative of the individual's brain electrical activity; continuously projecting, in real time, the obtained recording of electrical signal data onto a pre-determined ordering of a denoised optimal set wavelet packet atoms, to obtain a particular set of projections of the individual; continuously normalizing, in real time, the particular set of projections of the individual using a pre-determined set of normalization factors to form a set of normalized projections of the individual; continuously determining, in real time, at least one personalized mental state of the individual by assigning at least one specific brain state to the individual based on applying at least one machine learning algorithm to the set of normalized projections of the individual, where the at least one specific brain state is associated with a mental state, a neurological condition, or a combination of the mental state and the neurological condition; continuously determining a relationship between: i) the at least one physiological parameter, ii) the at least one environmental parameter, and iii) the at least one personalized mental state; continuously generating, in real time, an output, including: 1) a visual indication, where the visual indication is representative of the at least one personalized mental state, and 2) a feedback output which is configured to affect, based on the relationship, the at least one personalized mental state of the individual.

In some embodiments, the feedback output is selected from the group consisting of: an audible signal, a visual signal, a physically-sensed signal, and any combination thereof.

In some embodiments, the physically-sensed signal is a vibration that is physically sensed by the individual.

In some embodiments, the generating of the feedback output includes: determining a change beyond a pre-determined threshold in at least one of: i) the at least one physiological parameter, ii) the at least one environmental parameter, and iii) the at least one personalized mental state. In some embodiments, specific stimulation comprises deep brain, electric or chemical stimulation, or other electrical, magnetic, or ultrasound stimulation to elicit or alter a specific brain activity based on the collection of physiological measurements and the inferred brain state.

In some embodiments, the specifically programmed computer processor is further configured to determine the pre-determined ordering of the denoised optimal set wavelet packet atoms based on: obtaining from a plurality of individuals at least 100 recordings of electrical signal data representative of brain activity; obtaining an optimal set of wavelet packet atoms from the recorded electrical signal data from the recordings from the plurality of individuals, by: 1)
  selecting a mother wavelet selected from the group consisting of: Haar, Coiflet Daubehies, and Meyer wavelet families; 2) determining, by the specifically programmed processor, an optimal set of wavelet packet atoms, by: a) causing the at least one plurality of electrical signal data to be deconstructed into a plurality of wavelet packet atoms, using the selected mother wavelet; b) storing the plurality of wavelet packet atoms in at least one first computer data object; c) determining the optimal set of wavelet packet atoms using the pre-determined mother wavelet, and storing the optimal set of wavelet packet atoms in at least one second computer data object, where the determining is via utilizing a Coifman-Wickerhauser Best Basis algorithm; i) denoising the obtained optimal set of wavelet packet atoms from the recordings from the plurality of individuals; ii) reordering, the denoised optimal set of wavelet packet atoms from the recorded electrical signal data from the recordings from the plurality of individuals, to obtain a pre-determined ordering of the denoised optimal set of wavelet packet atoms from the recordings from the plurality of the individuals, by determining a minimum path, by: 1) projecting the at least one plurality of electrical signal data on to the denoised optimal set of wavelet packet atoms, to obtain a set of projections, where a projection is a result of a convolution of an electrical signal in each time window of the signal and a wavelet packet atom; 2) determining a collection of wire lengths for every data point within the set of projections, where each wire length is determined by a correlation of every two projections; 3) storing the collection of wire lengths for the set of projections in at least one third computer data object; 4) iteratively, determining, by the specifically programmed processor, a plurality of (i) orders of projections, and (ii) respective wire lengths, by i) determining the wire length for every data point in the projection by determining either the mean or sum of absolute distance of the statistical measure of the projections of different channels from their adjacent channels; and ii) storing the wire length data in at least one fourth computer data object; 5) determining, from the plurality of respective wire lengths, a particular order of projections that minimizes either the mean or sum of the wire lengths across the projections, across each 4 second window, and across all individuals within the plurality of individuals so as to identify the pre-determined ordered denoised optimal set of wavelet packet atoms; and creating the set of pre-determined normalization factors, and storing the pre-determined normalization factors in at least one fifth computer data object. In a particular embodiment thereof, the mother wavelet can also be optimized in accordance with Neretti et al. (2002).

In some embodiments, the visual indication includes a visual map, generated by: calculating a standard deviation of a time window of each normalized projection of the particular set of normalized projections of the particular individual, and assigning a color to each normalized projection of the particular set of normalized projections of the particular individual, based on the standard deviation of the time window of the respective projection.

In some embodiments, the correlation of every two projections is selected from the group consisting of: the mean of the sum of the absolute differences of the wavelet packet atoms, and a mean of the sum of (1−correlation) of the wavelet packet atoms.

In some embodiments, the apparatus includes two electrodes configured to record the electrical signal data representative of the individual's brain activity.

In some embodiments, when the individual is a child between years of 0 and 12.

In some embodiments, when the individual is a minimally conscious subject; the at least one personalized mental state is representative of a response of the minimally conscious subject to at least one stimulus; and the feedback output is at least one second stimulus configured to affect the minimally conscious subject.

In some embodiments, the least one environmental parameter is selected from the group consisting of: temperature, humidity, pressure, gravitational level, allergen level, and any combination thereof.

In some embodiments, the at least one machine learning algorithm is one of: logistic regression modeling algorithm, support vector machine modeling algorithm, and a deep learning modeling algorithm.

In some embodiments, the specifically programmed computer processor is further configured to perform at least the following operations: a) determining a first personalized mental state of the individual; b) generating a first visual indication, where the first visual indication is representative of the first personalized mental state; c) generating a first feedback output which is configured to affect, based on a first relationship, the first personalized mental state of the individual; where the first relationship is determined based on: i) at least one first physiological parameter, ii) at least one first environmental parameter, and iii) a first personalized mental state; d) determining, after subjecting the individual to the first feedback output, a second personalized mental state of the individual; e) generating a second visual indication, where the second visual indication is representative of the second personalized mental state; f) comparing the first visual indication and the second visual indication; g) generating a second feedback output which is configured to affect, based on a second relationship and a result of the comparing step, the second personalized mental state of the individual; where the second relationship is determined based on: i) at least one second physiological parameter, ii) at least one second environmental parameter, and iii) a second personalized mental state; repeating the steps a-g until at least one of: 1) a desired personalized mental state is obtained, 2) a first coherent response to the first feedback output is obtained, 3) a second coherent response to the second feedback output is obtained; and 4) any combination thereof.

In some embodiments, the first feedback output is at least one first reward.

In some embodiments, the second feedback output is at least one second reward.

In some embodiments, the present invention provides an exemplary inventive method that includes at least the following steps of: continuously obtaining, by a specifically programmed computer processor, a recording of electrical signal data representative of an individual's brain electrical activity; where the recording the electrical signal data representative of individual's brain electrical activity is received from an apparatus configured to be worn on an individual's head, and record: i) the individual's brain electrical activity, ii) at least one physiological parameter of the individual, selected from the group consisting of: heart rate, blood oxygen levels, body temperature, respiration rate, skin temperature, skin conductivity, and movement, and iii) at least one environmental parameter; continuously projecting, in real time, by the specifically programmed computer processor, the obtained recording of electrical signal data onto a pre-determined ordering of a denoised optimal set wavelet packet atoms, to obtain a particular set of projections of the individual; continuously normalizing, in real time, by the specifically programmed computer processor, the particular set of projections of the individual using a pre-determined set of normalization factors to form a set of normalized projections of the individual; continuously determining, in real time, by the specifically programmed computer processor, at least one personalized mental state of the individual by assigning at least one specific brain state to the individual based on applying at least one machine learning algorithm to the set of normalized projections of the individual, where the at least one specific brain state is associated with a mental state, a neurological condition, or a combination of the mental state and the neurological condition; continuously determining, by the specifically programmed computer processor, a relationship between: i) the at least one physiological parameter, ii) the at least one environmental parameter, and iii) the at least one personalized mental state; continuously generating, in real time, by the specifically programmed computer processor, an output, including: 1) a visual indication, where the visual indication is representative of the at least one personalized mental state, and 2) a feedback output which is configured to affect, based on the relationship, the at least one personalized mental state of the individual.

BRIEF DESCRIPTION OF THE FIGURES

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION OF THE INVENTION

Figure 1:
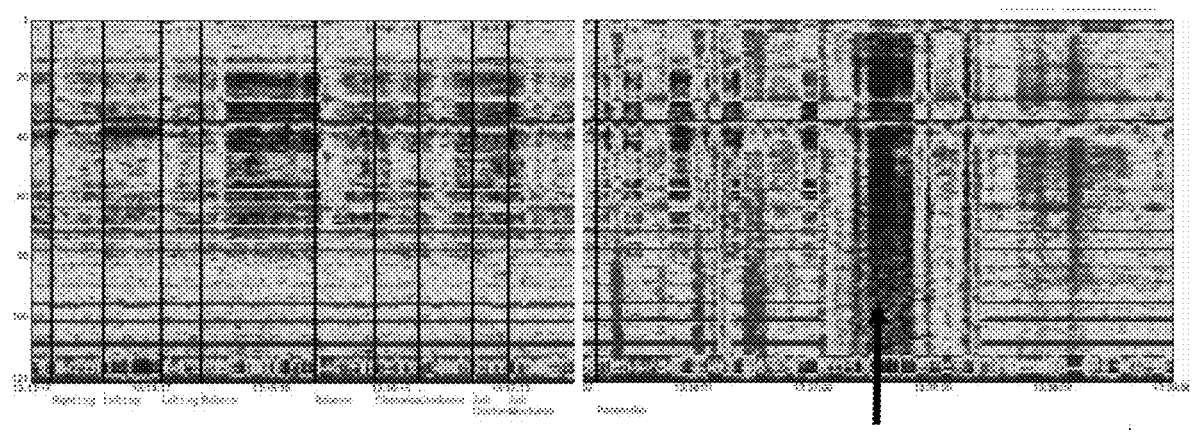
FIG. 1 shows a screenshot of an example of a representation of a recording of brain activity of a Parkinson's patient with and without active DBS at the Sub Thalamic Nucleus (STN).

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. In some embodiments, the terms "instantaneous," "instantaneously," "instantly," and "in real time" refer to a condition where a time difference between a first time when a search request is transmitted and a second time when a response to the request is received is no more than 1 second. In some embodiments, the time difference between the request and the response is between less than 1 second and several seconds.

As used herein, the term "dynamic(ly)" means that events and/or actions can be triggered and/or occur without any human intervention. In some embodiments, events and/or actions in accordance with the present invention can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

Brain stimulation is a viable complementary or stand-alone treatment for various brain disorders including, without limitation, brain injury, cognitive decline, Alzheimer's disease, Parkinson's disease, epilepsy, bulimia, depression, anxiety, attention disorders, impaired cognitive abilities, and chronic pain. Brain stimulation such as that described herein may also be used to enhance brain development. The stimulation itself may include invasive techniques, such as, for example, under the skull and deep brain stimulation as well as noninvasive techniques, such as, for example, electrical stimulation using alternating current (AC) and/or direct current (DC), magnetic stimulation, sound stimulation, ultrasound stimulation, optical stimulation, and oxygen based stimulation (e.g., treatment using a hyperbaric chamber). This large family of stimuli has a wide variety of parameters that can be personalized and optimized for a specific disorder and for an individual afflicted by the specific disorder.

In some embodiments, an invasive deep brain stimulation devices comprises at least one of a devices with electrodes providing a continuous or intermittent electrical or magnetic stimulation either deep into the brain, on the surface of the brain (under the skull), or close to or touching the vagus nerve (wherein the vagus nerve is close to the brain or remote from it); providing stimulation at or near the spinal cord; other penetrating methods for providing chemical compounds directly to a certain brain area; or providing light at a certain wavelength to a particular area of the brain.

In some embodiments, a non-invasive brain stimulator or stimulation device provides any kind of stimulation to any of the senses (tactile, taste, smell, audio, visual and combinations thereof); electric, magnetic, ultrasound, or chemical stimulation at different locations on the skull or locations on specific nerves, e.g. the vagus nerve in the ear, the median nerve on the hand, or nerves at the bottom of the feet.

The stimulation parameters may include:
- The location in or on the skull where the stimulation is provided, and the direction of the stimulatory beam
- The energy or current and duration of the stimulation
- The pattern of the stimulation (frequency or more complicated pattern)
- The number of stimuli, the duration, and the duration of intervals between stimuli (intermittent, discontinuous stimulation).

In some embodiments, the stimulation is triggered by a certain event, such as the onset of pre-ictal activity. Such abnormal electrical activity can be detected as described in WO 2016/132228 and U.S. Patent Application Publication No. 2017/0347906, the entire content of each of which is incorporated herein by reference.

The current state of the art in the optimization of the stimulation includes a pre-set or a collection of pre-set stimulation parameters. Optimization is then performed by either manually changing the preset parameters while observing or questioning the subject about how she feels. Such protocols are known in the art and described in, for example, U.S. Pat. No. 8,295,935, the entire content of which is incorporated herein by reference. Observation can tell whether the tremor is reduced, or dyskinesia is reduced. After the process of optimization with a neurologist or a stimulation expert is complete, the parameters are set.

In one embodiment the brain activity can be monitored continuously before and during the stimulation. In some embodiments, the brain activity can be detected by Neurosteer device such as those described in WO 2016/132228 and U.S. Patent Application Publication No. 2017/0347906 (the entire content of each of which is incorporated herein by reference), or with another EEG device, or fMRI or validated computerized scoring device such as that of CamCog (described in the world wide web at alz.org/media/documents/cognitive-assessment-toolkit.pdf).

The stimulation can be modified according to some schedule and the brain activity registered. Optimal stimulation parameters are then set based on achieving the desired brain activity.

In one embodiment, specific brain states such as fatigue, lack of attention, or poor cognitive functioning may be detected. In one embodiment, the brain state can be detected based on quantitative electroencephalography (qEEG) theory, such as determination of the increase in Delta energy, or reduction of Gamma. Then based on the determination of the specific condition, brain stimulation can be provided to activate the frontal lobe or to activate other areas based protocols known in the art of brain stimulation.

In a particular embodiment, a method for optimizing DBS for Parkinson's patients is presented.

Deep Brain Stimulation (DBS) includes one or more electrodes that are inserted surgically into the brain. There are several ways to determine the exact location of the stimulator using functional magnetic resonance imaging (fMRI) or multiple electrode electroencephalography (EEG). Stimulators may, for example, include long electrodes with multiple transmission sites thereon. Inclusion of multiple transmission sites facilitates altering the specific transmission pattern, location, and orientation of stimulation after surgical implantation using an external remote control. Current practice comprises clinical evaluation of the patient after implantation by a trained practitioner (e.g., a neurologist), on which basis stimulation parameters are optimized. The practitioner may, for example, evaluate the patient based on observing the patient at rest or participating in some activity to determine, for example, the amount of tremor (e.g., severity and/or frequency) or general behavior, physical palpation of a body part affected by the disease/condition (e.g., feeling the rigidity of the limbs), and/or asking the patient how he/she feels.

A tool for enabling post-operation optimization of DBS parameters is highly desired. Indeed, general monitoring and observing DBS effect on brain activity is important for achieving optimal clinical efficacy. Prior to the present inventor's discovery of the benefits of combinatorial therapy, wherein DBS is used in conjunction with brain activity monitoring as described herein, a clinical practitioner would essentially have to optimize DBS treatment empirically by trial and error, using the patient as an experimental test subject. In accordance with combinatorial methods described herein, the parameters of DBS can altered/modified using objective, rather subjective, indicators. As described herein, measuring brain activity in particular regions, for example, cognitive region A, as measured by detecting, for example, features from 20 to 60 offers an indicator of efficacy of DBS. See also U.S. Pat. No. 9,955,905, the entire content of which is incorporated herein by reference.

Figure 4:
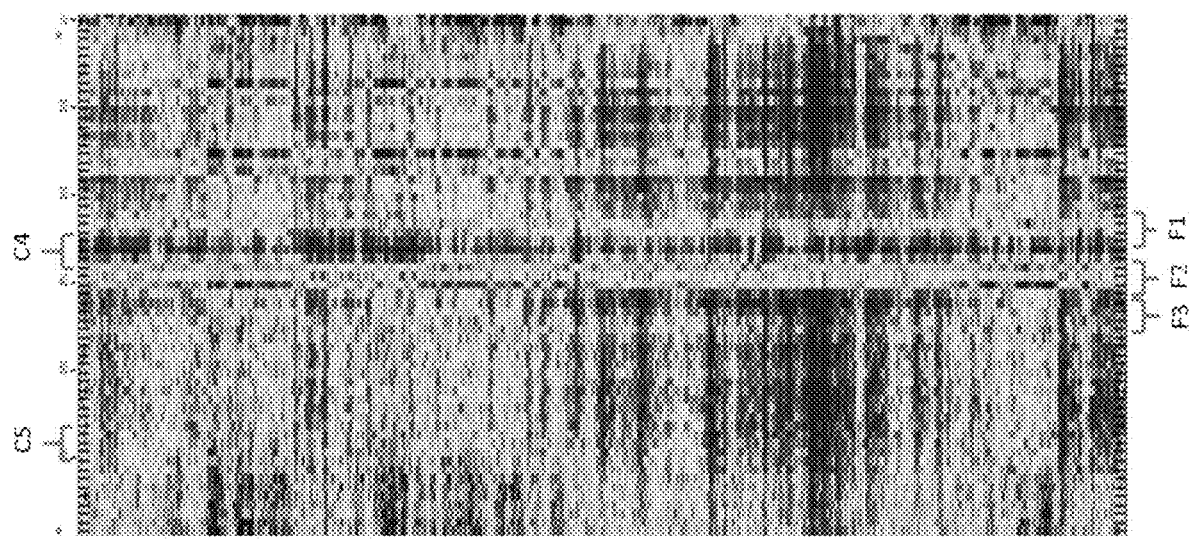
FIG. 4 shows a detailed sub-division of cognitive activity regions. The X-axis represents time, where the distance between the adjacent columns is 1 second. The Y-axis represents the different features or functional neural networks in the cognitive area and the "heat" color map represents the strength of activity of features so that blue is weak and red is strong. The level of activity is taken from the energy in the projection of the EEG signal onto the relevant feature at any given time.

With respect to cognitive region A, this region includes channels 10-60 in the graph depicted in FIG. 4 (channel numbers are approximate). Cognitive region A is subdivided into smaller strips as indicated in FIG. 4, each representing a different aspect of cognitive activity. These areas were found following studies pertaining to multiple cognitive tasks and multiple brain disorders. Cognitive load is related to the level of energy (represented by color) of different BAFs and to the number of different (cognitive) BAFs that are active during the task. The cognitive indications include (among others):
- Passive (e.g. listening) vs. active (e.g. calculating) activity can be separated.
- A sub-functionality division into short term and long-term memory activation biomarkers.
- The cognitive biomarker C1 which is a combination of the full 20 to 60 BAFs is active during almost every cognitive activity. It is also useful in distinguishing between levels of active (decision-making) vs. passive cognitive load as well as distinguishing between two types of anesthesia.
- The cognitive biomarkers C2, C3 and C4 may be active depending on the specific types of cognitive activity. For example, C3 is more active during long term memory tasks.
- C4 correlates with medial-prefrontal activity and is associated with execution and decision making. This region includes channels 35-40 in the graph. The executive region is more activated when subjects are engaged in decision-making. It is also active during sleep and during anesthesia. It may be active in some types of meditation and not in others. In general, activity in this region appear to be missing (or diminished) in subjects that are in coma. The biomarker C4 relates to activity in this region.

C5 (48-50) is a biomarker that differentiates between anesthetized and awake subjects. Moreover, it appears to be highly correlated with the difference between two types of anesthesia (volatile and TIVA, FIG. 3—First patent).

Regions F1 (30-34) and F2 (39-41) are most sensitive to stimulation of the frontal lobe via tDCS.

Region F3 (42-45) is another area indicating frontal lobe activity that appears to be less correlated with medial prefrontal activity. See, for example, Example 4.

Figure 5:
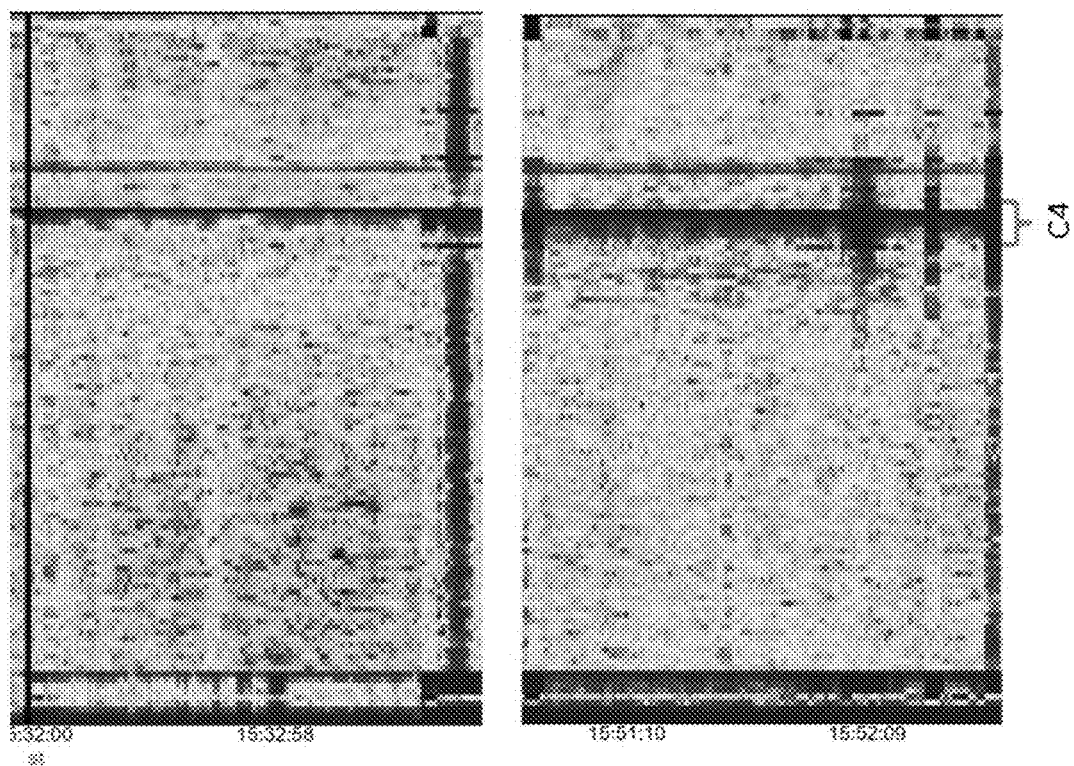
FIG. 5 shows a screenshot of a representation of recordings depicting the effect of 10 minutes of tDCS on specific cognitive regions. It indicates the strengthening of regions F1, F2, F3 and C4 from FIG. 4 following the frontal lobe stimulation via tDCS.
Figure 6:
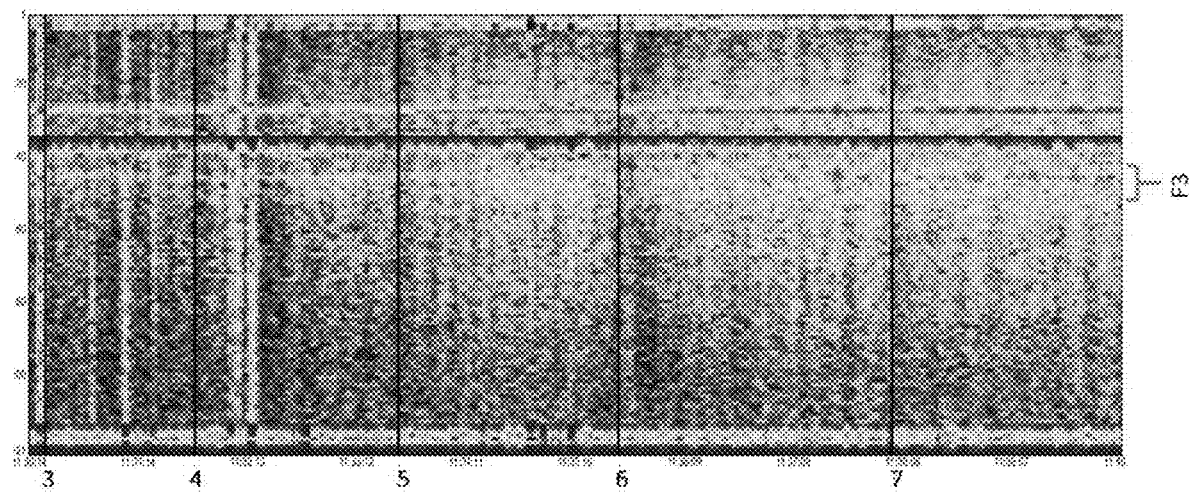
FIG. 6 shows a screenshot of a representation of recordings depicting the effect increased cognitive challenge (memorization of increasing number of digits) on specific cognitive regions and particularly shows that the biomarker F3 becomes more active during digit span task.
Figure 7:
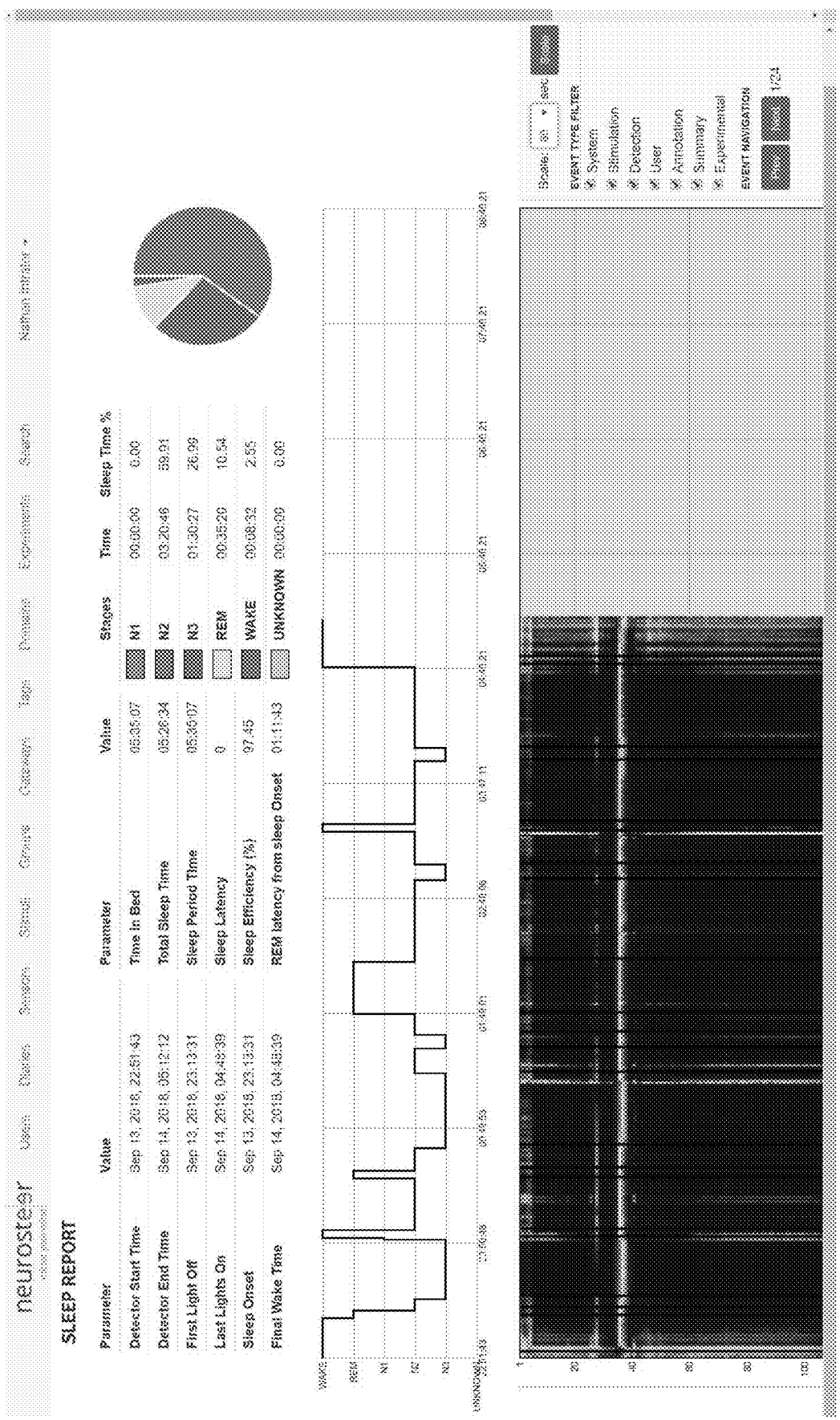
FIG. 7 depicts a sleep hypnogram that indicates the specific sleep stages. In a particular embodiment, a specific stimulation is used to increase the duration of the deep sleep state N3.

With regard to tDCS, the effect of stimulation is depicted in FIG. 5. More particularly, FIG. 5 shows the effect of 10 minutes of tDCS on the specific cognitive regions. FIG. 6 reveals that the biomarker F3 becomes more active during the digit span task, when a subject is requested to remember an increasing number of a digit as is marked at the x-axis of FIG. 6.

In accordance with combinatorial methods described herein, the parameters of DBS can also be changed dynamically during brain activity, for example, in the case of DBS used for treating epilepsy, where electrodes sense abnormal activity and may be used to react and counter abnormal activity. The specific embodiment describes a way to observe the effect of the DBS during specific motor and cognitive challenges, and provide an indication of determining the patterns which induce brain activity that is more desired, for example, closer to a brain activity of a healthy subject performing such tasks. Machine learning can be used to examine the brain activity patterns and determine automatically the more desired patterns. The described optimization method can be used for other aspects of DBS and said other types of stimulation.

Apparatus for Monitoring Brain Activity, Physiological Parameters, and Environmental Parameters In some embodiments, the present invention provides a system and method for monitoring detailed brain activity in an individual concurrently with monitoring the sensory environment so as to create a rich input/output relationship between the sensory environment and the related brain activity so as to detect states relating to normal and stimulated brain activity and brain malfunction.

In some embodiments, the apparatus is configured to be worn continuously. In some embodiments, the apparatus is configured to be worn while the individual is asleep. In some embodiments, the apparatus is configured to be worn while the individual is awake.

In one embodiment, the present invention provides a system comprising:
a. an apparatus configured to be worn on an individual's head, and record:
  i. the individual's brain electrical activity;
  ii. at least one physiological parameter of the individual, selected from the group consisting of: heart rate, blood oxygen and/or carbon dioxide levels, body temperature, respiration rate, skin temperature, skin conductivity, and movement; and
  iii. at least one environmental parameter, selected but not limited to the group consisting of: temperature, humidity, pressure, and allergen level;
b. a specifically programmed computer system, configured to (i) receive and process data corresponding to the individual's recorded brain activity, at least one recorded physiological parameter, and at least one recorded environmental parameter, and output, based on the processing, a visual indication of at least one personalized mental state of the particular individual, at least one personalized neurological condition of the particular individual, or both,
  wherein the visual indication of at least one personalized mental state of the particular individual, at least one personalized neurological condition of the particular individual, or both, is used to identify an underlying mental state, an underlying neurological condition, or a combination of an underlying mental state and an underlying neurological condition,
  wherein the system is configured to issue an alert if at least one of the underlying mental state, the underlying neurological condition, the combination of the underlying mental state and the underlying neurological condition, the at least one physiological condition, or the at least one environmental parameters changes beyond a pre-determined threshold.

In one embodiment, present invention provides a specifically programmed computer system including:
a. at least one specialized computer machine including:
  i. a non-transient memory, electronically storing particular computer executable program code; and
  ii. at least one computer processor which, when executing the particular program code, becomes a specifically programmed computer processor configured to perform at least the following operations:
    1. obtaining, in real-time, by a specifically programmed processor, electrical signal data representative of brain activity of a particular individual;
    2. processing, in real-time the electrical signal data representative of brain activity of a particular individual based upon an individual pre-determined predictor associated with a particular brain state, selected from a library of predictors containing a plurality of pre-determined predictors,
      wherein each individual pre-determined predictor is associated with a unique brain state,
      wherein the pre-determined predictor associated with a particular brain state comprises:
        i. a pre-determined mother wavelet,
        ii. a pre-determined representative set of wavelet packet atoms,
        iii. a pre-determined ordering of wavelet packet atoms, created from the pre-determined mother wavelet, and
        iv. a pre-determined set of normalization factors,
      wherein the processing comprises:
        i. causing, by the specifically programmed processor, the electrical signal data to be deconstructed into a plurality of pre-determined deconstructed wavelet packet atoms, utilizing the pre-determined representative set of wavelet packet atoms,
          wherein time windows of the electrical signal data are projected onto the pre-determined representative set of wavelet packet atoms
          wherein the projection is via convolution or inner product, and
          wherein each pre-determined representative wavelet packet atom corresponds to a particular pre-determined brain activity feature from a library of a plurality of pre-determined brain activity features;

ii. storing the plurality of pre-determined deconstructed wavelet packet atoms in at least one computer data object;
iii. causing, by the specifically programmed processor, the stored plurality of pre-determined deconstructed wavelet packet atoms to be re-ordered within the computer data object, based on utilizing a pre-determined order;
iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and
3. outputting, a visual indication of at least one personalized mental state of the particular individual, at least one personalized neurological condition of the particular individual, or both, based on the processing,
wherein an individual pre-determined predictor associated with a particular brain state within the plurality of pre-determined predictors is generated by the steps consisting of:
i. obtaining the pre-determined representative set of wavelet packet atoms by:
1. obtaining from a plurality of individuals, by the specifically programmed processor, at least one plurality of electrical signal data representative of a brain activity of a particular brain state;
2. selecting a mother wavelet from a plurality of mother wavelets,
wherein mother wavelet is selected from a wavelet family selected from the group consisting of: Haar, Coiflet Daubehies, and Mayer wavelet families; optimization of the mother wavelet may also be determined in accordance with Neretti et al. (2002), the entire content of which is incorporated herein by reference;
3. causing, by the specifically programmed processor, the at least one plurality electrical signal data to be deconstructed into a plurality of wavelet packet atoms, using the selected mother wavelet;
4. storing the plurality of wavelet packet atoms in at least one computer data object;
5. determining, an optimal set of wavelet packet atoms using the pre-determined mother wavelet, and storing the optimal set of wavelet packet atoms in at least one computer data object,
wherein the determining is via utilizing a Best Basis algorithm; and
6. applying, by the specifically programmed processor, wavelet denoising to the number of wavelet packet atoms in the optimal set;
ii. obtaining the pre-determined ordering of wavelet packet atoms by:
1. projecting, by the specifically programmed processor, the at least one plurality of electrical signal data representative of a brain activity for each 4 second window of the data onto the pre-determined representative set of wavelet packet atoms;
2. storing the projections in at least one computer data object;
3. determining, by the specifically programmed processor, the wire length for every data point in the projection by determining the mean absolute distance of the statistical measure of the projections of different channels from their adjacent channels;
4. storing the wire length data in at least one computer data object; and
5. re-ordering the stored projections, by the specifically programmed computer to minimize a statistical value of the wire length value across each time window, and across all individuals within the plurality of individuals, and across the projections; and
iii. obtaining the pre-determined set of normalization factors by:
1. determining, by the specifically programmed computer, the mean and standard deviation of the values of the stored projections.

In one embodiment, the present invention provides a computer implemented method including:
a. obtaining, in real-time, by a specifically programmed processor, electrical signal data representative of brain activity of a particular individual;
b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state,
wherein the pre-determined predictor associated with a particular brain state includes:
i. a pre-determined mother wavelet,
ii. a pre-determined representative set of wavelet packet atoms, created from the pre-determined mother wavelet,
iii. a pre-determined ordering of wavelet packet atoms, and
iv. a pre-determined set of normalization factors,
wherein the processing includes:
i. causing, by the specifically programmed processor, the electrical signal data to be deconstructed into a plurality of pre-determined deconstructed wavelet packet atoms, utilizing the pre-determined representative set of wavelet packet atoms,
wherein time windows of the electrical signal data are projected onto the pre-determined representative set of wavelet packet atoms
wherein the projection is via convolution or inner product, and
wherein each pre-determined representative wavelet packet atom corresponds to a particular pre-determined brain activity feature from a library of a plurality of pre-determined brain activity features;
ii. storing the plurality of pre-determined deconstructed wavelet packet atoms in at least one computer data object;
iii. causing, by the specifically programmed processor, the stored plurality of pre-determined deconstructed wavelet packet atoms to be re-ordered within the computer data object, based on utilizing a pre-determined order;

iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and c. outputting, a visual indication of at least one personalized mental state of the particular individual, at least one personalized neurological condition of the particular individual, or both, based on the processing,
wherein the individual pre-determined predictor associated with a particular brain state from within the plurality of pre-determined predictors is generated by the steps including:
i. obtaining the pre-determined representative set of wavelet packet atoms by:
a. obtaining from a plurality of individuals, by the specifically programmed processor, at least one plurality of electrical signal data representative of a brain activity of a particular brain state;
b. selecting a mother wavelet from a plurality of mother wavelets,
wherein the mother wavelet is a member of a wavelet family selected from the group consisting of: Haar, Coiflet Daubehies, and Mayer wavelet families optimization of the mother wavelet may also be determined in accordance with Neretti et al. (2002), the entire content of which is incorporated herein by reference;
c. causing, by the specifically programmed processor, the at least one plurality electrical signal data to be deconstructed into a plurality of wavelet packet atoms, using the selected mother wavelet;
d. storing the plurality of wavelet packet atoms in at least one computer data object;
e. determining, an optimal set of wavelet packet atoms using the pre-determined mother wavelet, and storing the optimal set of wavelet packet atoms in at least one computer data object,
wherein the determining is via utilizing analysis Best Basis algorithm; and
f. applying, by the specifically programmed processor, wavelet denoising to the number of wavelet packet atoms in the optimal set;
ii. obtaining the pre-determined ordering of wavelet packet atoms by:
a. projecting, by the specifically programmed processor, the at least one plurality of electrical signal data representative of a brain activity for each 4 second window of the data onto the pre-determined representative set of wavelet packet atoms;
b. storing the projections in at least one computer data object;
c. determining, by the specifically programmed processor, the wire length for every data point in the projection by determining the mean absolute distance of the statistical measure of the projections of different channels from their adjacent channels;
d. storing the wire length data in at least one computer data object; and
e. re-ordering the stored projections, by the specifically programmed computer to minimize a statistical value of the wire length value across each time window, and across all individuals within the plurality of individuals, and across the projections; and
iii. obtaining the pre-determined set of normalization factors by:
a. determining, by the specifically programmed computer, the mean and standard deviation of the values of the stored projections.

In one embodiment, the computer implemented method further comprises:
a. obtaining, in real-time, by a specifically programmed processor, data representative of (i) at least one physiological parameter of the individual, selected from the group consisting of: heart rate, blood oxygen and/or carbon dioxide levels, body temperature, respiration rate, skin temperature, skin conductivity, and movement, and (ii) at least one environmental parameter; and
b. determining a relationship between the obtained data and the visual indication of at least one personalized mental state of the particular individual, at least one personalized neurological condition of the particular individual, or both.

In one embodiment, each time window is a four second time window.

In one embodiment, the statistical value for the re-ordering is the mean of the sum of the absolute differences of the wavelet packet atoms or a mean of the sum of (1−correlation) of the wavelet packet atoms.

In one embodiment, the visual indication of at least one personalized mental state of the particular individual is used to identify an underlying mental state, an underlying neurological condition, or a combination of an underlying mental state and an underlying neurological condition, in the particular individual, wherein the specifically programmed computer utilizes at least one machine learning algorithm, which includes, but is not limited to logistic regression modeling, support vector machine modeling, and a deep learning modeling, to assign at least one specific brain state to the visual indication of at least one personalized mental state of the particular individual, wherein the at least one specific brain state is associated with a mental state, a neurological condition, or a combination of a mental state and a neurological condition.

In one embodiment, the assignment of at least one specific brain state to the visual indication of at least one personalized mental state of the particular individual identifies an abnormality in at least one neural network in the brain of the particular individual associated with a particular neurological condition.

In one embodiment, the abnormality in at least one neural network in the brain of the particular individual is used to diagnose the particular individual having a neurological condition.

In one embodiment, the neurological condition is selected from the group consisting of, Alzheimer's disease, dementia, stress, fatigue, anxiety, epilepsy, traumatic brain injury, partial loss of cognitive function, migraine, chronic pain, perceived pain (e.g., such as that associated with phantom limb pain), post-traumatic stress disorder (PTSD), acute pain, coma, a lack of response, or inappropriate response to external stimuli associated with autism, or autism spectrum disorders, obsessive compulsive disorders (e.g., bulimia and anorexia nervosa), a lack of concentration, psychiatric disorders, and sleep disorders.

As is understood in the art, tremors or involuntary small movements of, e.g., the hands or fingers are associated with different neurological disorders, most notably Parkinson's (hands are at rest) and essential tremor (hands are not at rest). Tremors can also be caused or enhanced by fatigue, stress, anxiety and other emotional states.

The term "motor dysfunction" is used herein to refer to a family of disorders affecting muscles that include different involuntary movements, or movements that do not conform to a symmetric movement, e.g. limping. Such disorders may be a result of nerve damage associated with or caused by, e.g., a stroke or brain injury; or by abnormal nerve activity associated with, for example, epilepsy; or by other syndromes associated with abnormal brain development such as Tourette syndrome.

Dyskinesia is a form of motor dysfunction, where some parts of the body, generally the upper limbs do not rest and are typically moving widely (in contrast to the small movements associated with small tremor). Dyskinesia is mostly frequently associated with Parkinson's disease.

Gate freeze is a known form of Parkinson's disorder, where a movement, most often walking, freezes and the person cannot continue and move the leg from its position for a certain period of time. As a result, gate freeze disrupts walking.

Mood swings and other psychiatric condition swings correspond to rapid changes in mood or other conditions such as energy level, fatigue, anxiety, attention or even personality. The mood can change from depression and even suicidal attempts to a normal or exceedingly happy mood with outbursts of laughter or other indications of happiness. In both cases, the environment is interpreted very differently, so the same sentence can cause laughter in one case and anger in another.

Attention disorders correspond to a family of disorders wherein attention cannot be retained for extended periods of time. Attention disorders are typically associated with either hyperactivity of particular brain regions, or with a lethargic condition of sluggishness and lack of energy. Attention disorders may be associated with anxiety, fear, mood and other cognitive or emotional states.

Sleep disorders include those wherein one or more sleep stages occur with less intensity and/or less frequently than in the general population. Examples of sleep disorders are associated with, for example, difficulty falling asleep, and multiple awake periods during the night, wherein long awake periods may be related to anxiety and other disorders and very short awake periods are frequently associated with sleep apnea.

Cognitive disorders include attention disorders, as well as retention of short, long, or working memory. Cognitive disorders may be associated with impaired conversion of short term memory to long term memory, and/or with retention or recall of memories. Cognitive disorders may also be associated with impaired decision making, deduction and otherwise proper assessment of the collection of input and ability to integrate them into a coherent reality.

With respect to any of the above diseases, disorders, or conditions, the source of the dysfunction provides an indication of the potential nature of alleviating the dysfunction, for example, if the source is epileptic, then a stimulation attempting to reduce the epileptic activity may be used to advantage. If the source is Parkinsonian, then a stimulation attempting to alleviate Parkinsonian symptoms, for example, via DBS in the sub thalamic nucleolus STN may be used to reduce dyskinesia. In general, analysis of brain activity and detection of brain activity that can be viewed as abnormal (not found in brain activity of a group of individuals classified as healthy subjects performing similar tasks) presents guidance regarding stimulation used to treat a disease or disorder and optimization of the stimulation.

In one embodiment, the at least one specific brain state is used to determine the emotional state of the particular individual.

In one embodiment, the particular individual is receiving a therapy, and the visual indication of at least one personalized mental state of the particular individual is used to determine the effectiveness of the therapy.

In one embodiment, the particular individual is receiving a therapy, and the visual indication of at least one personalized mental state of the particular individual is used to determine the nature of the therapy to be administered.

In one embodiment, the particular individual is receiving a therapy, and the visual indication of at least one personalized mental state of the particular individual is used to determine the duration of the therapy.

In one embodiment, the particular individual is receiving a therapy, and the visual indication of at least one personalized mental state of the particular individual is used to determine the dosing regimen of the therapy.

In one embodiment, the therapy is an anesthetic agent, and the effectiveness of the anesthetic is determined by the particular individual's ability to feel pain and/or the individual's perceived pain level and the correlation to the change in the visual indication of at least one personalized mental state of the particular individual.

In one embodiment, the therapy is a migraine therapy, and the effectiveness of the migraine therapy is determined by the particular individual's ability to feel pain, and/or the individual's perceived pain level and the correlation to the change in the visual indication of at least one personalized mental state of the particular individual.

In one embodiment, the particular individual is performing a specific cognitive task.

In one embodiment, the specific cognitive task is selected from the group including short and/or long term memory recall, e-learning, meditation, and concentration.

In one embodiment, the particular individual has a particular brain state at a certain time.

In one embodiment, the present invention provides a method,
wherein the method induces a change in the mental state, neurological condition, or both of a subject from a first mental state, first neurological condition, or both, to a desired mental state, desired neurological condition, or both, the method comprising:
a. obtaining a first visual indication of a first mental state, first neurological condition, or both, of a subject;
b. applying at least one first stimulus to the subject and obtaining a second visual indication of a second mental state, second neurological condition, or both, of the subject;
c. determining if the second visual indication of a second mental state, second neurological condition, or both, of the subject is indicative of the desired mental state, second neurological condition, or both, and if not;
d. iteratively,
i. applying at least one subsequent stimulus to the subject,
wherein each at least one subsequent stimulus is different from the preceding at least one stimulus;

ii. obtaining a subsequent visual indication of a mental state, neurological condition, or both, of the subject;
iii. determining if the subsequent visual indication of the mental state, neurological condition, or both, of the subject is indicative of the desired mental state, desired neurological condition, or both,
wherein steps i to iii are performed until the desired mental state, desired neurological condition, or both, is obtained.

In one embodiment, the present invention provides a method,
wherein the method induces a change in the mental state, neurological condition, or both, of a subject from a first mental state, first neurological condition, or both, to a desired mental state, desired neurological condition, or both, the method comprising:
a. obtaining a first visual indication of a first mental state, first neurological condition, or both of a subject;
b. applying at least one first stimulus to the subject and obtaining a second visual indication of a second mental state, second neurological condition, or both of the subject;
c. determining if the second visual indication of a second mental state, second neurological condition, or both of the subject is indicative of the desired mental state, desired neurological condition, or both, and if not;
d. iteratively,
i. comparing the first visual indication of a first mental state, first neurological condition, or both of the subject to the second visual indication of a second mental state, second neurological condition, or both of the subject;
ii. based on the comparison, selecting a subsequent stimulus and applying the selected subsequent stimulus to the subject,
wherein each at least one subsequent selected stimulus is different from the preceding at least one stimulus;
iii. obtaining a subsequent visual indication of a mental state, neurological condition, or both of the subject;
iv. determining if the subsequent visual indication of the mental state, neurological condition, or both of the subject is indicative of the desired mental state, desired neurological condition, or both,
wherein steps i to iv are performed until the desired mental state, desired neurological condition, or both, is obtained.

In some embodiments, BAF representations are further analyzed to identify features that are repeatedly observed in a subject's visual representation of brain activity in response to an at least one stimulus. For example, Let B(j,t) be a matrix of BAF where the rows j go from 1 to 121 in case of 121 BAFs, and the columns t represent time with steps of one second, namely the BAF vectors is being updated every 1 sec. In some embodiments, the rows that are more correlated are ordered geographically closer to one another, so the brain activity values in row j are more correlated to those in row j+1 than to those in row j+2, under some measure of correlation over a large data set that was used to determine the BAFs.

There is also a labeling L(t) which labels what happened during the recording of each time column. Thus, it is possible to build predictors to specific events that occurred during the time the BAF data was collected, and it is possible to cluster the columns of the matrix in a supervised (looking at the labels) or unsupervised way, like in k-means clustering. Furthermore, it is possible to cluster only part of the matrix namely only several of the BAFs. This enables to find those channels that produce a more coherent set of clusters from the data, namely they produce a set of cluster centers where the activity in a specific set of channels often falls into one of the cluster centers, namely the actual activity is not far (by some measure such as Euclidian distance) from the activity represented by the cluster center.

In some embodiments, the clusters are named, to indicate the BAF channels where they came from, and the actual cluster center that was found in those channel: for example, one feature, by way of illustration can be named 1320_15, to indicate that the cluster corresponds to channels 13 to 20 and it is ordinal cluster 15 that was found in that set of BAFs. This actual name can be considered a certain letter in a novel alphabet that can be found in brain activity after the interpretation into BAFs.

Given this alphabet, in some embodiments, one can then look at letters which are highly correlated, namely clusters from different channels which co-occur at high probability. Then such letters can be combined into a single letter. This is done after building a covariance matrix of all letters found, and then based on them combining letters with a correlation above a preset threshold.

In some embodiments, once a minimal alphabet is found (after combining highly correlated letters) one can look at words that are being formed, namely a collection of several letters that occur together. Also, in some embodiments, grammatical rules can be inferred using, for example, Markov modeling, namely inference of letters/words which occur in a sequence at high probability. Bayesian modeling, or graphical modeling may be used in some embodiments for inference of hidden structures of letter/words.

All said inference can now be used together with the labeling to determine a correlation of the inferenced brain response and the events that occurred while the BAFs were recorded. Once such correlation is found, we assume that there was a coherent brain response to the stimulus and can then record the stimuli which produced a coherent brain response.

Based on the coherent response, we can determine the response to the stimuli which we term RtS.

In one specific embodiment, RtS can help indicate the type of stimuli that a person that is in a Minimal Conscious State (MCS) responds to. For example, it can help determine whether the person responds in a consistent way to visual stimuli, auditory stimuli, other sensory stimuli, commands etc.

In some embodiments, RtS can indicate the degree of minimal consciousness the person is in, can help optimize medical intervention that aims to increase response to various stimuli. In the case of a person in MCS, in some embodiments, one can look at the entropy of the said alphabet and produce a single number which determines the total entropy of the alphabet (just based on letters or also based on more sophisticated grammatical rules that are inferred and length of words that are inferred.

In a specific embodiment, the group of channels 34-38 which have been found to be missing in MCS can be used as a neural feedback to encourage MCS subjects to increase the activity of these channels.

In another embodiment, the creation of an alphabet and entropy inference from the alphabet can be done in a totally unlabeled (unsupervised) manner. This can be useful when determining the degree of brain damage, such as, for example, of a baby that was born during an ischemic episode, namely a baby that was born while the mother suffered a transient ischemic attack.

In one embodiment, a temporal structure probabilistic model is applied to the BAF's to determine the correlation between the at least one stimulus applied and the observed brain activity. In some embodiments, a strong correlation indicates a coherent response to the at least one stimulus.

In some embodiments, the apparatus is configured to be worn for minutes, hours or days. In some embodiments, the apparatus is configured to be worn for up to 24 hours. In some embodiments, the apparatus is configured to be worn for up to 23 hours. In some embodiments, the apparatus is configured to be worn for up to 22 hours. In some embodiments, the apparatus is configured to be worn for up to 21 hours. In some embodiments, the apparatus is configured to be worn for up to 20 hours. In some embodiments, the apparatus is configured to be worn for up to 19 hours. In some embodiments, the apparatus is configured to be worn for up to 18 hours. In some embodiments, the apparatus is configured to be worn for up to 17 hours. In some embodiments, the apparatus is configured to be worn for up to 16 hours. In some embodiments, the apparatus is configured to be worn for up to 15 hours. In some embodiments, the apparatus is configured to be worn for up to 14 hours. In some embodiments, the apparatus is configured to be worn for up to 13 hours. In some embodiments, the apparatus is configured to be worn for up to 12 hours. In some embodiments, the apparatus is configured to be worn for up to 11 hours. In some embodiments, the apparatus is configured to be worn for up to 10 hours. In some embodiments, the apparatus is configured to be worn for up to 9 hours. In some embodiments, the apparatus is configured to be worn for up to 8 hours. In some embodiments, the apparatus is configured to be worn for up to 7 hours. In some embodiments, the apparatus is configured to be worn for up to 6 hours. In some embodiments, the apparatus is configured to be worn for up to 5 hours. In some embodiments, the apparatus is configured to be worn for up to 4 hours. In some embodiments, the apparatus is configured to be worn for up to 3 hours. In some embodiments, the apparatus is configured to be worn for up to 2 hours. In some embodiments, the apparatus is configured to be worn for up to 1 hour.

In some embodiments, the data collected by the apparatus can alert the individual or, alternatively, a caregiver in real time.

In some embodiments, the data collected by the apparatus is stored for offline data analysis.

Without intending to be limited to any particular theory, detecting changes in cognitive abilities, as well as changes in emotional status at home can provide early indications on such changes, which can lead to quick intervention. Without intending to be limited to any particular theory, the earlier the intervention is, the better results can be obtained from the intervention and the lower the cost of the intervention.

In some embodiments, the present invention provides a system comprising:
  a. an apparatus configured to be worn on an individual's head, and record:
    i. the individual's brain electrical activity;
    ii. at least one physiological parameter of the individual, selected from the group consisting of: heart rate, blood oxygen and/or carbon dioxide levels, body temperature, respiration rate, skin temperature, skin conductivity, and movement; and
    iii. at least one environmental parameter;
  b. a specifically programmed computer system, configured to (i) receive and process data corresponding to the individual's recorded brain activity, at least one recorded physiological parameter, and at least one recorded environmental parameter, and output, based on the processing, a visual indication of at least one personalized mental state of the particular individual, at least one personalized neurological condition of the particular individual, or both,
    wherein the visual indication of at least one personalized mental state of the particular individual, at least one personalized neurological condition of the particular individual, or both, is used to identify an underlying mental state, an underlying neurological condition, or a combination of an underlying mental state and an underlying neurological condition,
    wherein the system is configured to issue an alert if at least one of the underlying mental state, the underlying neurological condition, the combination of the underlying mental state and the underlying neurological condition, the at least one physiological condition, or the at least one environmental parameters changes beyond as pre-determined threshold.

In some embodiments, the at least one physiological parameter includes, but is not limited to: heart rate, blood oxygen and/or carbon dioxide levels, body temperature, respiration rate, skin temperature, skin conductivity, and movement.

In some embodiments, the at least one physiological parameter is galvanic skin response.

In some embodiments, the apparatus includes a potential pulse oximeter.

In some embodiments, the apparatus includes a 3-D accelerometer, which can be worn on the body for general movement, on the legs for gait disorders, or on the hands for tremor management.

In some embodiments, the at least one environmental parameter includes, but is not limited to: oxygen concentration, temperature, humidity, carbon monoxide levels, carbon dioxide levels, and the like.

In some embodiments, the apparatus is configured to record at least one of the following physiological and cognitive parameters from the individual:
1. Sleep level;
2. Sleep stage;
3. Heart rate;
4. Heart rate variability;
5. Cardiac arrhythmia;
6. Cardiac Contractility and cardiac output
7. Blood oxygen and/or carbon dioxide levels;
8. Temporal pulse wave morphology with indications of blood pressure changes (Future);
9. Bit to bit respiration timing and overall respiration rate;
10. Skin temperature and conductivity; or
11. Posture position, movement level, walking and climbing on stairs, sudden fall, lack of movement An apparatus according to some embodiments of the present invention may include the following elements:
EEG and/or EOG sensors
EEG reference sensor, there are two such sensors above the two eyes
Temperature sensor
Pulse wave pressure sensor touching the frontal branch of the superficial temporal artery
3D Accelerometers
Pulse or pulse oximeter (infrared) sensor Battery, electronic circuitry and wireless communication behind the ear Pressure sensor Skin conductance sensor EMG and/or EOG Ear phone Microphone Environmental monitors to provide sensory information in the immediate vicinity of the subject. These include but are not limited to temperature, pressure, humidity which are attached to the sensor suite but are not touching the subject's head.

In some embodiments, the apparatus includes all or some of the above mentioned sensors mounted on the strap or around the ear. In some embodiments, the data collected from the sensors is stored and analyzed on a processor on the sensor which includes cellular communication capabilities. The main processor may be on a nearby cellphone, for example. In some embodiments, the collective sensory information is fused with additional information collected by the cellular processor. Such information includes geographic location, communication with nearby smart devices such as car, home, school or office environment.

In some embodiments, analysis of the data is performed in real-time to obtain:
1) Detection of anomalies, namely activity outside the regular area of activity of the collection of sensors and sensory environment, for a certain part of the sensory input data, e.g. brain malfunction during driving at high temperature;
2) Creation of an organ activity profile from the collection of sensory information. This includes the pulse and hemodynamic activity, as well as vital signs such as temperature and skin conductance. It can be used for statistics collection, or for disease management, such as in sleep or alert time monitoring. Detection of brain malfunctions responsive to particular sensory environments may occur alongside other changes such as an increase in blood pressure;
3) Specific patterns which are indicative of specific states, such as concentration, mood, sleep level, certain desire (e.g. to move a limb, or to purchase a product) are calculated from the collective sensory information and are registered. If needed, potential alerts are created, for example, if sleep is detected during driving; and/or
4) Other alerts can be sent to relatives, care givers or other interested parties depending on certain presets of the device. These may include but are not limited to medical alerts of falls, a condition which may pose medical risk, such as epileptic seizure, or sleep at a certain time of day.

Implications of the combined sensory environment and brain activity monitoring relate to mood change detection, attention disorder, or sudden lack of attention, cognitive malfunction and potential medical problems related to hemodynamic parameters such as high or low blood pressure, affecting the said relationship.

In some embodiments, apparatus of the present invention is used to determine the individual's sleep patterns. In some embodiments, changes in an individual's sleep patterns may indicate the onset of a disease or condition. Examples of the disease or condition include, but are not limited to: PTSD, stroke, dementia, Alzheimer's disease, Parkinson's disease, concussion, traumatic brain injury, brain tumor, brain swelling, stress, malnutrition, COPD, sleep apnea, cardiac disease, intoxication, poisoning, hypoxia, and the like.

In some embodiments, the apparatus of the present invention is used in the management of a chronic disease of an individual. Examples of chronic diseases suitable for management using an apparatus according to some embodiments of the present invention include, but are not limited to: epilepsy, depression, Alzheimer's disease, OCS, PTSD, ADD, and the like.

In some embodiments, the apparatus of the present invention is used in the management of an acute disease of an individual. Examples of acute diseases suitable for management using an apparatus according to some embodiments of the present invention include, but are not limited to: concussion, traumatic brain injury, stroke, and the like.

In some embodiments, the apparatus of the present invention is used in the management of post-traumatic stress disorder (PTSD), a condition that afflicts some people following a traumatic experience. It is generally correlated with an inability to recover following a traumatic experience and is typified by ongoing sensations of intense stress and fear, even when considerable time has passed since the traumatic event. PTSD is associated with over-activity of the sympathetic system. PTSD can manifest as a chronic, ongoing condition or a short term, acute condition. Symptoms typically manifest within three months of the traumatic event, but the delay in onset can be years. To be diagnosed with PTSD, an adult must present with all of the following symptoms for at least a month: at least one re-experiencing symptom, at least one avoidance symptom, at least two arousal and reactivity symptoms, and at least two cognition and mood symptoms. Re-experiencing symptoms include flashbacks of the traumatic experience, bad dreams, and frightening thoughts. Avoidance symptoms include avoiding places, events, and/or objects that remind the patient of the traumatic experience and avoiding thoughts or feelings pertaining to the traumatic experience. Arousal and reactivity symptoms include a hyper-active startle reflex, feeling tense or nervous, difficulty sleeping, and a tendency to angry outbursts. Cognition and mood symptoms include difficulty recalling key features of the traumatic event, a negative self-image or overall world image, and distorted feelings like guilt or blame. PTSD is frequently associated with depression, substance abuse, anxiety disorders (e.g., panic disorder), and/or suicidal thoughts and/or attempts.

Treatments implemented for subjects afflicted with PTSD include pharmaceutic intervention, and/or psychotherapy ("talk" therapy). Pharmaceutical intervention may, for example, call for administration of antidepressants to a subject afflicted PTSD. Antidepressants and other medications may be administered in conjunction with psychotherapy. Other medications, such as Prazosin, which is a sympatholytic drug used to treat high blood pressure, anxiety, and panic disorders, have also shown efficacy for the treatment of specific PTSD symptoms. Prazosin is an alpha-adrenergic blocker that is specific for the alpha-1 receptors. Although not currently approved by the Food and Drug Administration (FDA) for the treatment of PTSD, research indicates that Prazosin alleviates sleep problems, particularly nightmares, which are commonly experienced by PTSD patients. Persons of skill in the art refer to the FDA website for the latest information on patient medication guidelines, warnings, and newly approved medications for the treatment of PTSD.

Psychotherapy, which is sometimes referred to as "talk therapy", typically calls for regular and progressive counseling sessions wherein a PTSD patient talks in depth with a mental health professional. Psychotherapy may involve one-on-one or group therapy sessions. Talk therapy treatment for PTSD usually lasts 6 to 12 weeks, but it can last longer as required. Research has, furthermore, shown that support from family and friends can be an important part of recovery. Some forms of psychotherapy target the symptoms of PTSD directly, while others focus on social, family, and/or job-related problems. A skilled practitioner may choose to combine different therapies depending on each person's needs.

Cognitive behavioral therapy (CBT) has been shown to confer therapeutic benefit to patients afflicted with PTSD. CBT may, for example, include: exposure therapy, whereby patients are trained to face and control their fear; and cognitive restructuring, whereby patients are trained to process and interpret the memories of the traumatizing event. Exposure therapy, for example, gradually exposes them to the trauma they experienced, but in a safe and controlled way. Exposure therapy uses mental visualization, writing, and/or visiting the place where the event happened and, in so doing, the therapist better enables patients with PTSD to cope with their feelings. Cognitive restructuring seeks to assist PTSD patients in more accurately understanding the traumatic event. In many circumstances, PTSD patients ascribe guilt and responsibility for the traumatic event to themselves and thereby amplify the emotional distress associated therewith. Cognitive restructuring helps the PTSD patient revisit the traumatic experience in a more realistic way.

While PTSD is considered as a binary state, namely one either has the condition or not, it is in fact a wide spectrum of disorders in which the cognitive functioning of the brain is distracted by over activity of the emotional part. Detection of such over emotional activity as well as detection of cognitive sub-functioning or distraction is of great importance for various methods of treatment. The spectrum of over activated emotional networks includes stress, anxiety, mood disorders, and attention problems as well as executive commands.

The technology and methods described herein may, for example, be used to track over-activity of the sympathetic system for diagnostic purposes and/or to provide indications as to the therapeutic efficacy of a medical intervention implemented for the treatment of PTSD. The technology and methods described herein may further be used to track over emotional activity as well as detection of cognitive sub-functioning or distraction. The spectrum of over activated emotional networks includes stress, anxiety, mood disorders, and attention problems as well as executive commands. Parameters that may be adjusted using the technology and methods described herein include indications as to the desired duration of therapy, type of therapy or combinations thereof, and assessment of therapeutic efficacy on an ongoing basis.

In some embodiments, the apparatus of the present invention is used in the management of pain, which may for example be general, chronic, acute, perceived, and/or migraine pain. The spectrum of over activated emotional networks includes stress, anxiety, mood disorders, and attention problems as well as executive commands. Parameters that may be adjusted using the technology and methods described herein include indications as to the desired duration of therapy, type of therapy or combinations thereof, and assessment of therapeutic efficacy on an ongoing basis.

In some embodiments, the apparatus of the present invention is used in the management of phantom pain refers to a type of perceived pain that can range from mild to extreme. Phantom pain generally relates to pain that is perceived to emanate from a peripheral body part that has been severed from main body. One example of phantom pain is phantom limb pain, which relates to mild to extreme pain experienced in the area of main body from which the severed limb was excised. Limb amputations may occur via accidental means or may be medically recommended to prolong or preserve a subject's life (e.g., circumstances wherein an amputation is required to remove a limb riddled with cancer cells or to remove a gangrenous limb) or to improve the quality of a subject's life (e.g., circumstances wherein an amputation is required to remove a body part that is a chronic source of pain). Phantom limb pain typically disappears or decreases over time, but when the condition persists for more than six months, the prognosis for improvement is poor.

Phantom limb pain is thought to be caused by the ongoing signaling of nerve endings at the site of the amputation, whereby pain signals continue to be transmitted to the brain such that the brain perceives that the limb is still attached to the main body. The brain's memory of pain may, furthermore, be retained and is interpreted as pain in a manner independent of signals from injured nerves. In addition to pain, some people experience sensations of tingling, cramping, heat, and/or cold that are perceived to emanate from the portion of the limb that was removed.

Medical intervention for the treatment of phantom limb pain is challenging and depends on the subject's level of pain. Treatments include, for example, heat application, biofeedback to reduce muscle tension, relaxation techniques, massage of amputated stump, injections of local anesthetics and/or steroids in the amputated stump, nerve blocks, surgery to remove scar tissue potentially entangling a nerve, physical therapy, transcutaneous electrical nerve stimulation (TENS) of the stump, neurostimulation techniques such as spinal cord stimulation or deep brain stimulation, and/or medications such as pain relievers, neuroleptics, anticonvulsants, antidepressants, beta-blockers, and sodium channel blockers.

The technology and methods described herein may, for example, be used to monitor the amputee's brain activity responsive to ongoing signaling of nerve endings at the site of the amputation and/or the brain's memory of pain for diagnostic purposes and/or to provide indications as to the therapeutic efficacy of a medical intervention implemented for the treatment of, for example, phantom limb pain. Parameters that may be adjusted using the technology and methods described herein include indications as to the desired duration of therapy, type of therapy or combinations thereof, and assessment of therapeutic efficacy on an ongoing basis. The technology can monitor pain, can indicate the onset or strengthening of the feeling of pain and can thus be used to alert the patient and caregiver, initiate or suggest timely usage of drugs or pain releasing stimuli and be part of a system that can alter the lifestyle to reduce the overall feeling of pain. All this accounts for all types of pain, migraine, and anxiety attacks as well as epileptic activity and seizures.

Further to the above, the technology and methods described herein may be used to monitor an individual's brain activity, and other physiological parameters, and environmental parameters, to correlate the monitored brain activity with the physiological and environmental parameters, and from the correlation, to detect changes in the individual's cognitive ability and/or brain state. As described herein, such correlations may be used to diagnose a condition or disorder in a subject and/or to provide indications as to the therapeutic efficacy of a medical intervention implemented for the treatment of the condition or disorder in the subject. Parameters that may be adjusted using the technology and methods described herein include indications as to the desired duration of therapy, type of therapy or combinations thereof, and assessment of therapeutic efficacy on an ongoing basis.

Determination of the Subject's Mental State, Neurological Condition, or Both

Decomposing EEG signals into different components is an effective tool to study brain activity and brain states, and deducing the role of certain functional regions of the brain, or neural networks in the brain for a given brain state. Without being limited by any particular theory, a particular brain state is associated with a particular mental state, a particular neurological condition, or a particular combination of a mental state and a neurological condition.

Without being intended to be limited by any particular theory, brain activity, detected via conventional EEG, is associated with a number of frequency bands from around 0.5 Hz (Delta waves) to Gamma waves which are above 32 Hz. In between are Theta, Alpha, and Beta waves, among others. However, it is assumed EEG electrodes are only sensitive to electrical signals which emanate from a small region of the brain, close to each electrode. Consequently, it is customary to record EEG activity with a large number of electrodes which cover the whole head. The location of the brain responsible for the detected electrical activity is calculated by estimating the phase of the electrical signal as it arrives to different electrodes. The BAFs described above may include these frequency bands as well.

In some embodiments of the present invention, the determining the role of certain regions or neural networks within the brain for a given cognitive function or mental state is not required. In some embodiments, the electrical activity of the brain of a subject is recorded using two electrodes (e.g., Fp1 and Fp2) located on the forehead of the subject. In some embodiments, either the Fp1, or the Fp2 electrode is used as a reference electrode, and the recorded electrical activity is the difference in between the Fp1 and Fp2 electrode. Alternatively, in some embodiments, the FpZ electrode may be used as either the reference or recording electrode.

In some embodiments, the present invention provides a computer implemented method including:
- a. obtaining, in real-time, by a specifically programmed processor, electrical signal data representative of brain activity of a particular individual;
- b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state,
  wherein the pre-determined predictor associated with a particular brain state includes:
    - i. a pre-determined mother wavelet,
    - ii. a pre-determined representative set of wavelet packet atoms, created from the pre-determined mother wavelet,
    - iii. a pre-determined ordering of wavelet packet atoms, and
    - iv. a pre-determined set of normalization factors,
  wherein the processing includes:
    - i. causing, by the specifically programmed processor, the electrical signal data to be deconstructed into a plurality of pre-determined deconstructed wavelet packet atoms, utilizing the pre-determined representative set of wavelet packet atoms,
      wherein time windows of the electrical signal data are projected onto the pre-determined representative set of wavelet packet atoms
        wherein the projection is via convolution or inner product, and
      wherein each pre-determined representative wavelet packet atom corresponds to a particular pre-determined brain activity feature from a library of a plurality of pre-determined brain activity features;
    - ii. storing the plurality of pre-determined deconstructed wavelet packet atoms in at least one computer data object;
    - iii. optionally causing, by the specifically programmed processor, the stored plurality of pre-determined deconstructed wavelet packet atoms to be re-ordered within the computer data object, based on utilizing a pre-determined order;
    - iv. obtaining a statistical measure of the activity of each of the re-ordered plurality of pre-determined deconstructed wavelet packet atoms; and
    - v. normalizing the re-ordered plurality of pre-determined wavelet packet atoms, based on utilizing a pre-determined normalization factor; and
      - a. outputting, a visual indication of at least one personalized mental state of the particular individual, at least one personalized neurological condition of the particular individual, or both, based on the processing,
  wherein the individual pre-determined predictor associated with a particular brain state from within the plurality of pre-determined predictors is generated by the steps including:
    - i. obtaining the pre-determined representative set of wavelet packet atoms by:
      - a. obtaining from a plurality of individuals, by the specifically programmed processor, at least one plurality of electrical signal data representative of a brain activity of a particular brain state;
      - b. selecting a mother wavelet from a plurality of mother wavelets,
        wherein mother wavelet is selected from an wavelet family selected from the group consisting of: Haar, Coiflet Daubehies, and Mayer wavelet families, optimization of the mother wavelet may also be determined in accordance with Neretti et al. (2002), the entire content of which is incorporated herein by reference;
      - c. causing, by the specifically programmed processor, the at least one plurality electrical signal data to be deconstructed into a plurality of wavelet packet atoms, using the selected mother wavelet;
      - d. storing the plurality of wavelet packet atoms in at least one computer data object;
      - e. determining, an optimal set of wavelet packet atoms using the pre-determined mother wavelet, and storing the optimal set of wavelet packet atoms in at least one computer data object,
        wherein the determining is via utilizing a Best Basis algorithm; and
      - f. applying, by the specifically programmed processor, wavelet denoising to the number of wavelet packet atoms in the optimal set;
    - ii. obtaining the pre-determined ordering of wavelet packet atoms by:

a. projecting, by the specifically programmed processor, the at least one plurality of electrical signal data representative of a brain activity for each 4 second window of the data onto the pre-determined representative set of wavelet packet atoms;
b. storing the projections in at least one computer data object;
c. determining, by the specifically programmed processor, the wire length for every data point in the projection by determining the mean absolute distance of the statistical measure of the projections of different channels from their adjacent channels;
d. storing the wire length data in at least one computer data object; and
e. optionally re-ordering the stored projections, by the specifically programmed computer to minimize a statistical value of the wire length value across each time window, and across all individuals within the plurality of individuals, and across the projections; and
iii. obtaining the pre-determined set of normalization factors by:
a. determining, by the specifically programmed computer, the mean and standard deviation of the values of the stored projections.

In some embodiments, the computer implemented method further comprises:
a. obtaining, in real-time, by a specifically programmed processor, data representative of (i) at least one physiological parameter of the individual, selected from the group consisting of: heart rate, blood oxygen and/or carbon dioxide levels, body temperature, respiration rate, skin temperature, skin conductivity, and movement, and (ii) at least one environmental parameter; and
b. determining a relationship between the obtained data and the visual indication of at least one personalized mental state of the particular individual, at least one personalized neurological condition of the particular individual, or both.

In some embodiments, the electrical signal data representative of brain activity of a particular individual is recorded using two electrodes located on the forehead of the particular individual.

In some embodiments, the electrical activity of the brain of a subject is recorded using between one and three electrodes located on the forehead of the subject. In some embodiments, the electrical activity of the brain of a subject is recorded using between one and three electrodes located at region(s) of the head which is/are other than or in addition to the forehead of the subject. For example, in some embodiments, at least one electrode is located behind or on, or in an ear of the subject. For example, in some embodiments, at least one electrode is part of an item positioned on the head of the subject, where the item is configured for at least one additional function in addition to hosting the at least one electrode. For example, in some embodiments, the item is a headwear piece (e.g., hat). For example, in some embodiments, the item is an electronic device (e.g., headphones).

In some embodiments, the item positioned on the head of the subject further comprises at least one sensor selected from the group consisting of: an accelerometer, a gyroscope, a pulse meter, an oximeter, a pressure sensor, a heart rate monitor, and a temperature sensor.

In some embodiments, the item positioned on the head of the subject is further configured to detect at least one physiological parameter selected from the group consisting of: EEG, fNIRS, GSR, facial expression, muscle tone, temperature, heart rate, blood flow, blood oxygen and/or carbon dioxide levels, blood inflation level, blood coagulation level, heart rate variability, blood flow morphology, and head acceleration.

In some embodiments, the electrical activity of the brain of a subject is recorded according to the methods disclosed in G. Castellani, et al., Frontiers in Genetics Vol 5, pg 1-12 (2014).

In some embodiments, the electrical signal data representative of brain activity of a particular individual is recorded with a sufficiently large sampling rate above 250 and a dynamic range configured to detect sufficient cortical activity in the desired location of the brain. For example, a larger dynamic range is expected to detect more cortical activity than a smaller dynamic range. In one embodiment, the dynamic range is 15 bit resolution of the analog-to-digital (A/D) and above.

In some embodiments, the particular individual is performing a specific cognitive task.

In some embodiments, the specific cognitive task is selected from the group including short and/or long term memory recall, e-learning, meditation, and concentration.

In one embodiment, the particular individual has a particular brain state at a certain time.

Processing the Recorded Electrical Signal Data Representative of Brain Activity of a Particular Individual According the Method of Some Embodiments Described Herein Deconstructing the recorded electrical signal data representative of brain activity of a particular individual: In some embodiments, the recorded electrical signal data representative of brain activity of a particular individual is recorded in real-time over a certain time period. In some embodiments, the electrical signal data representative of brain activity of a particular individual is recorded for up to one hour. In some embodiments, the electrical signal data representative of brain activity of a particular individual is recorded for up to 50 minutes. In some embodiments, the electrical signal data representative of brain activity of a particular individual is recorded for up to 40 minutes. In some embodiments, the electrical signal data representative of brain activity of a particular individual is recorded for up to 30 minutes. In some embodiments, the electrical signal data representative of brain activity of a particular individual is recorded for up to 20 minutes. In some embodiments, the electrical signal data representative of brain activity of a particular individual is recorded for up to 10 minutes.

In some embodiments, the real-time recorded electrical signal data representative of brain activity of a particular individual is deconstructed into a plurality of pre-determined deconstructed wavelet packet atoms, utilizing a pre-determined representative set of wavelet packet atoms. Each individual pre-determined deconstructed wavelet packet atom within the plurality of pre-determined deconstructed wavelet packet atoms corresponds to a brain activity feature ("BAF").

In some embodiments, the a pre-determined representative set of wavelet packet atoms is created from a pre-determined mother wavelet, selected from an wavelet family selected from the group including, but not limited to: Haar, Coiflet Daubehies, and Mayer wavelet families. Other wavelet families suitable for mother wavelets according to some embodiments of the present invention are described in the website located on the world wide web at mathworks.com/ help/wavelet/ref/waveletfamilies. In a particular embodiment, optimization of the mother wavelet may also be determined in accordance with Neretti et al. (2002), the entire content of which is incorporated herein by reference In some embodiments, recorded electrical signal data representative of brain activity of a particular individual is deconstructed into a plurality of pre-determined deconstructed wavelet packet atoms, utilizing a pre-determined representative set of wavelet packet atoms according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition based on Shannon equation as detailed in section III. Entropy of a vector.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Coifman and Wickerhauser 1992 whose such specific disclosure is incorporated herein by reference.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Neretti and Intrator, 2002, whose such specific disclosure is incorporated herein by reference.

Re-ordering the plurality of pre-determined deconstructed wavelet packet atoms: In some embodiments, the plurality of pre-determined wavelet packet atoms is reordered, according to a pre-determined order. In some embodiments, the re-ordered plurality of pre-determined wavelet packet atoms, is normalized, utilizing a pre-determined normalization factor. In some embodiments, the plurality of pre-determined wavelet packet atoms is only normalized.

In some embodiments, utilizing electrical data recorded via standard EEG recording electrodes, the exemplary specifically programmed processor of the present invention is programmed to first normalize each wavelet packet atom, outputted by at least one band-pass filter, separately based on a dataset of collected data from multiple individuals to determine the distribution of the representation values for each of the wavelet packet atoms separately. In some embodiments, the at least one band-pass filter has 2-36 channels. In some embodiments, the at least one band-pass filter has at least 12 channels. In some embodiments, the at least one band-pass filter has at least 16 channels. In some embodiments, the at least one band-pass filter has at least 32 channels.

The Visual Indication of at Least One Personalized Mental State of the Particular Individual: In some embodiments, the normalized, re-ordered plurality of a statistical measure of projections onto pre-determined wavelet packet atoms is assembled into a visual representation, wherein each individual normalized pre-determined wavelet packet atom in the plurality, corresponds to a BAF, and is arranged in the representation according the pre-determined order. As used herein, a "BAFs representation" refers to a visual representation of the normalized, re-ordered plurality of pre-determined projections onto wavelet packet atoms.

In some embodiments, the BAFs representation of the particular individual has 121 individual BAFs. Alternatively, in some embodiments, the BAFs representation of the particular individual has up to 200 individual BAFs. Alternatively, in some embodiments, the BAFs representation of the particular individual has from 10 to 200 individual BAFs. Alternatively, in some embodiments, the BAFs representation of the particular individual has from 1 to 1000 individual BAFs. Alternatively, in some embodiments, the BAFs representation of the particular individual has from 30 to 1000 individual BAFs. Alternatively, in some embodiments, the BAFs representation of the particular individual has at least 30 individual BAFs. Alternatively, in some embodiments, the BAFs representation of the particular individual has a number of individual BAFs which is a multiple (e.g., 2×, 3×, 4×, 5×, 6×, etc.) of a number BAFs being recorded.

In some embodiments, the BAFs representation of the subject has 121 individual BAFs. Alternatively, in some embodiments, the BAFs representation of the subject over 200 individual BAFs. Alternatively, in some embodiments, the BAFs representation of the subject has from 10 to 200 individual BAFs. Alternatively, in some embodiments, the BAFs representation of the subject has from 1 to 1000 individual BAFs. Alternatively, in some embodiments, the BAFs representation of the subject has from 30 to 1000 individual BAFs. Alternatively, in some embodiments, the BAFs representation of the subject has at least 30 individual BAFs. Alternatively, in some embodiments, the BAFs representation of the subject has a number of individual BAFs which is a multiple (e.g., 2×, 3×, 4×, 5×, 6×, etc.) of a number of neural networks being analyzed. In some embodiments, the BAFs include traditional EEG recordings.

In such recordings, each line perpendicular to the y axis represents an activity of a projection onto a single pre-determined wavelet packet atom, (also referred to herein as a BAF). For example, the activity can be represented via at least one suitable statistical measurement of a projection onto a single wavelet packet atom or a group of wavelet packet atoms, where the suitable statistical measurement can be, but not limited to, mean, standard deviation, and the like. In some embodiments, the BAFs representation can be color coded. For example, various activity area(s) on an intensity spectrum can be presented, for example but not limited to, by presenting high activity area(s) as more darkly shaded regions of at least one particular color ("hot") to low activity tends area(s) as more lighted shaded region(s) of the at least one color or at least one other color ("cold"), and any continuous shading in between based on corresponding activity level. Each column perpendicular to the x axis represents a vector of brain activity state (the BAFs representation) at a specific time or specific time period. Thus, the x axis is measured in time (e.g., milliseconds, seconds, minutes, hours, days, etc.). In some embodiments, the image is normalized by a suitable non-linear transformation such as, for example, histogram equalization, prior to the color coding each brain activity (BAF) of the plurality of BAFs.

In some embodiments, the exemplary specifically programmed processor of the present invention is programmed to cluster the electrical signal data representative of brain activity of a particular individual before a pre-determined predictor is determined. For example, the exemplary specifically programmed processor of the present invention is programmed to generate a collection of m-dimensional vectors from projections on in pre-determined deconstructed wavelet packet atoms which can be further clustered into different brain states. In some embodiments, the exemplary specifically programmed processor of the present invention is programmed to determine a number of brain states by using at least one machine learning technique. For example, the exemplary specifically programmed processor of the present invention is programmed to utilize hierarchical clustering to analyze the clustered data and to decide which clusters to group together based on the relative distance between their members.

In some embodiments, the exemplary specifically programmed processor of the present invention is programmed to utilize the cluster membership construct the plurality of pre-determined predictors based, at least in part, on:
1) the distance from a cluster center or from different members of the cluster, and/or
2) a sequence of cluster membership that preceded the current frame.

For example, the exemplary specifically programmed processor of the present invention is programmed to utilize at least one temporal model (e.g., but not limited to, a Markov chain, a hidden Markov model, other similarly suitable models) based on the cluster membership to determine a particular predictor of the library of predictors.

In some embodiments, after the cluster membership is assigned to each window frame, the exemplary specifically programmed processor of the present invention is programmed to generate at least one temporal structure probabilistic model. For example, in text analysis, from the data, the exemplary specifically programmed processor of the present invention is programmed to: construct the vocabulary of letters (specific clusters); identify words based on segmentation of letters, construct the words vocabulary from the identified words, and, interpret particular grammatical rules to create sentences from the words. For example, the first step is to construct a matrix of probability to move from one letter to the other.

In some embodiments, the temporal structure probabilistic model is used to determine the correlation between the at least one stimulus applied and the observed brain activity. In some embodiments, a strong correlation indicates a coherent response to the at least one stimulus.

In some embodiments, the degree of response ("RtS") is used to identify the at least one stimulus that the subject is capable of responding to. By way of illustration, RtS determine whether the subject responds in a consistent way to visual stimuli, auditory stimuli, other sensory stimuli, commands etc.

Identification of an Underlying Mental State, an Underlying Neurological Condition, or a Combination of an Underlying Mental State and Neurological Condition According the Method of Some Embodiments Described Herein In some embodiments, the visual indication of at least one personalized mental state of the particular individual is used to identify an underlying mental state, an underlying neurological condition, or a combination of an underlying mental state and an underlying neurological condition, in the particular individual, wherein the specifically programmed computer utilizes at least one machine learning algorithm selected from the group consisting of logistic regression modeling, support vector machine modeling, and a deep learning modeling, to assign at least one specific brain state to the visual indication of at least one personalized mental state of the particular individual, wherein the at least one specific brain state is associated with a mental state, a neurological condition, or a combination of a mental state and a neurological condition.

In some embodiments, the exemplary specifically programmed processor of the present invention is programmed to identify an underlying mental state, an underlying neurological condition, or a combination of an underlying mental state and an underlying neurological condition, in the particular individual utilizing at least one machine learning algorithm such as, but not limited to, logistic regression modeling, support vector machine modeling, and a deep learning modeling. Specifically, in some embodiments, the exemplary specifically programmed processor of the present invention is programmed to execute at least the following steps:
1) separating the electrical signal data representative of brain activity of a particular individual into training, validation and test data sets;
2) generating a family of models based on the training set, adjusted based on the validation set;
3) testing the performance of each model on the test set;
4) repeating steps 1-3 for different parameters of a particular AI model (e.g. the regularization parameter in a ridge regression model; the number of hidden units in a feed forward neural network; the weight decay parameter in a feed forward neural network; types and a number of kernels in a kernel model such as support vector machine; a combination of Gaussians and the regularization parameters in a support vector machine; a combination of Gaussians models; etc.); and
5) after a set of model parameters is determined, obtaining prediction results on a new data set and repeat the steps 1-4 for different families of orthogonal decomposition and other model parameters obtained from the recorded electrical signal data representative of brain activity of a particular individual.

In some embodiments, electrical signal data representative of brain activity of a particular individual is recorded when the particular individual has a particular mental state. In some embodiments, the particular mental state is unknown, and the methods according to some embodiments of the present invention are utilized to identify the particular mental state.

Examples of the particular mental state include, but are not limited to, seizure, fear, anxiety, pain, sleep states (e.g. REM sleep), awake, alert, fatigue, anaesthetized, meditation states, stress, other moods, different brain states associated with dementia, a lack of response, or inappropriate response to external stimuli associated with autism, or autism spectrum disorder, and the like.

In some embodiments, the electrical signal data representative of brain activity of a particular individual is recorded when the particular individual is performing a specific cognitive task. In some embodiments, the methods according to some embodiments of the present invention identify an underlying mental state, an underlying neurological condition, or a combination of an underlying mental state and an underlying neurological condition, based, at least in part, on the electrical signal data representative of brain activity of a particular individual recorded while the particular individual is performing the specific cognitive task.

Examples of the specific cognitive task include, but are not limited to, short and long term memory recall, identification of stimuli, meditation, learning, watching a movie, observing images, intense concentration during motor operation, response to a sensory stimulus, and the like.

In some embodiments, the sensory stimulus can be auditory, tactile, olfactory, visual, and the like.

In some embodiments, the assignment of at least one specific brain state to the visual indication of at least one personalized mental state of the particular individual identifies an abnormality in at least one neural network in the brain of the particular individual associated with a particular neurological condition.

In some embodiments, the abnormality in at least one neural network in the brain of the particular individual is used to diagnose the particular individual having a neurological condition.

In some embodiments, the neurological condition is selected from the group consisting of, Alzheimer's disease, dementia, stress, fatigue, anxiety, epilepsy, traumatic brain injury, PTSD, loss of cognitive function, coma, a lack of response, or inappropriate response to external stimuli associated with autism, or autism spectrum disorders, a lack of concentration, and sleep disorders.

In some embodiments relating to sleep disorders, stimulation in the range between 1 to 4 Hz (a part of the delta range) may assist in falling asleep quickly or increasing the duration of a deep sleep stage. In one embodiment, DC stimulation (tDCS) on the forehead at location Fp1 and Fp2 can stimulate the frontal lobe and improve attention and cognitive functioning. In general, a stimulation that includes a DC level to stimulate a general activity in a certain region and on top of that, an AC stimulation at a specific frequency, such as theta or alpha or beta, can elicit specific attention, or integration between sensory modalities. In general, stimulation will be optimized to produce a desired brain state response, and above examples, should be viewed as initial stimuli patterns from which optimization may be determined as described herein.

In some embodiments, Parkinson's disease activity is, for example, related to a reduction in cognitive activity in specific cognitive functions such as working and short term memory deposit and recall. Parkinson's disease is also associated with exaggerated activity in the emotional BAFs. See also the right-hand side of FIG. 1.

In some embodiments, tremor, motor dysfunction, dyskinesia, and gate freeze are associated with Parkinson's disease activity, wherein general activity is exaggerated. See, for example, FIG. 3 which depicts elevated activity associated with gate freeze.

In some embodiments, epilepsy is associated with continuous activity of specific BAFs as is shown, for example, in FIG. 4.

In some embodiments, brain activity associated with migraine headaches and other brain states associated with pain are illustrated in Example 4 of US 2016/0235351 A1, the entire content of which is incorporated herein by reference.

Figure 3:
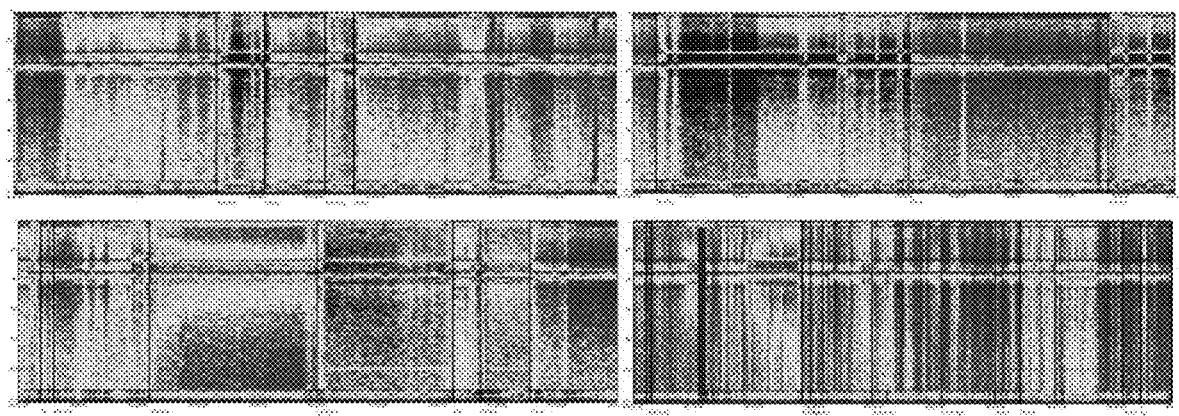
FIG. 3 shows a screenshot of a representation of recordings of four examples of 10 minutes of brain activity. There is an excessive brain activity, which may occur in some neurological disorders such as Parkinson's, Alzheimer's, TBI, dementia or frontal lobe dysfunction. The excessive activity can be characterized by high (brown/red) activity level in all or most of the brain activity features (BAFs) and for an extended period of time (at least few minutes).

In some embodiments, anxiety is associated with exaggerated brain activity, as is illustrated in FIG. 3, bottom right.

In some embodiments, depression is associated with minimal response to specific cognitive and emotional stimuli. One illustrative example of brain activity associated with depression is presented in FIG. 3, bottom left in the middle (blue area).

In some embodiments, sleep is associated with brain activity related to specific sleep stages and the relationship between the specific sleep stages. Indeed, the relationship between the specific sleep stages provide important guidance for optimizing brain stimulation. Brain activity related to specific sleep stages is illustrated in Example 5 of US 2016/0235351 A1, the entire content of which is incorporated herein by reference In some embodiments, cognitive response of a short term type is depicted in FIG. 5, wherein brain activity following 10 minutes of brain stimulation comprising tDCS to the frontal lobe is depicted. Individuals with attention disorders will in general exhibit a reduction in brain activity indicative of cognitive response, whereas cognitive response should stay high or get even higher in an individual not afflicted with an attention disorder. FIG. 6 depicts an increase in cognitive activity resulting from an increase in the cognitive challenge. In the case of attention deficit, a reduction is typically seen instead.

In some embodiments, the particular individual's neurological condition is unknown, and the methods according to some embodiments of the present invention identify the neurological condition.

In some embodiments, the at least one specific brain state is used to determine the emotional state of the particular individual.

In some embodiments, the particular individual is receiving a therapy, and the visual indication of at least one personalized mental state of the particular individual is used to determine the effectiveness of the therapy.

For example, by way of illustration, early intervention in autism patients, at around 6 months of age can improve the treatment of autism. In another example, an earlier detection of abnormal activity in at least one neuronal network that is associated with epilepsy in the brain of an individual can improve the treatment of epilepsy, or warn the individual, or the individual's care giver that a seizure is occurring, or will occur. In another example, an earlier detection of abnormal activity in at least one neuronal network that is associated with migraine in the brain of an individual can improve the treatment of migraine, or warn the individual, or the individual's care giver that a migraine is occurring, or will occur. In another example, an earlier detection of abnormal activity in at least one neuronal network that is associated with an ischemic event in the brain of an individual can improve the treatment of ischemic injury, or warn the individual, or the individual's care giver that an ischemic event, such as, for example, a transient ischemic event, or stroke is occurring, will occur, or has occurred. In some embodiments, the brain activity of the particular individual may be recorded whilst the subject is asleep, which, in the case of certain ischemic conditions, is when such conditions are more likely to occur.

In some embodiments, the particular individual is receiving a therapy, and the visual indication of at least one personalized mental state of the particular individual is used to determine the nature of the therapy to be administered.

In some embodiments, the particular individual is receiving a therapy, and the visual indication of at least one personalized mental state of the particular individual is used to determine the duration of the therapy.

In some embodiments, the particular individual is receiving a therapy, and the visual indication of at least one personalized mental state of the particular individual is used to determine the dosing regimen of the therapy.

In some embodiments, the therapy is an anesthetic agent, and the effectiveness of the anesthetic is determined by the particular individual's ability to feel pain and/or the individual's perceived pain level and the correlation to the change in the visual indication of at least one personalized mental state of the particular individual.

In some embodiments, the therapy is a migraine therapy, and the effectiveness of the migraine therapy is determined by the particular individual's ability to feel pain, and/or the individual's perceived pain level and the correlation to the change in the visual indication of at least one personalized mental state of the particular individual.

In some embodiments, the migraine therapy is a medication. Alternatively, in some embodiments, the migraine therapy is guided imagination. Alternatively, in some embodiments, the migraine therapy is hypnosis. Alternatively, in some embodiments, the migraine therapy is meditation.

In some embodiments, in contrast to the analysis of fetal brain activity using Amplitude Integrated EEG which typically detects the two brain conditions of sleep and awake states, and the dynamics of shift from one state to the other to identify the degree of brain damage, the exemplary specifically programmed processor of the present invention is programmed to perform group analysis on a group of brain states of infants, and determine the brain states of the infant at a certain time.

In another example, in neural marketing, in some embodiments, the exemplary specifically programmed processor of the present invention is programmed to perform group analysis on a group of brain states in individuals receiving a stimulation at each time frame, and to determine the proportions in the group that are in the same brain state at a given window frame. This enables to measure the engagement of the group with the stimulation, as when a larger portion of the group is found in the same brain state, it is likely that this happens due to the stimulation, thus the group is considered to be engaged and reacting to the stimuli. The specific brain state, at which a portion of the group is in, can correspond to the specific reaction to the stimuli, allowing for feedback training.

In some embodiments, the methods of the present invention determine a mental state of a particular individual at a first time point. In some embodiments, brain of the particular individual changes from one mental state to another, but remains in a first mental state for the majority of the time. In some embodiments, the first mental state is not favorable. In some embodiments, the system may supply a stimulus that encourages the brain of the particular individual to enter a second, more favorable mental state, via neural feedback. For example, by way of illustration, the particular individual may be in a coma, and the first mental state may be a state of non-responsiveness. The system may supply a stimulus that encourages the brain of the particular individual to enter a second, more responsive mental state.

In another example, the patient may have an autism spectrum disorder, and the first mental state may be the individual refusing, or being unable to maintain eye contact with another person. The system may supply a stimulus that encourages the brain of the particular individual to enter a second mental state where the individual is more easily capable of maintaining eye contact.

The Plurality of Pre-Determined Predictors

In some embodiments, an individual pre-determined predictor associated with a particular brain state within the plurality of pre-determined predictors is generated by the steps including:
i. obtaining the pre-determined representative set of wavelet packet atoms by:
a. obtaining from a plurality of individuals, by the specifically programmed processor, at least one plurality of electrical signal data representative of a brain activity of a particular brain state;
b. selecting a mother wavelet from a plurality of mother wavelets,
wherein mother wavelet is selected from an wavelet family selected from the group consisting of: Haar, Coiflet Daubehies, and Mayer wavelet families, optimization of the mother wavelet may also be determined in accordance with Neretti et al. (2002), the entire content of which is incorporated herein by reference;
c. causing, by the specifically programmed processor, the at least one plurality of electrical signal data to be deconstructed into a plurality of wavelet packet atoms;
d. storing the plurality of wavelet packet atoms in at least one computer data object;
e. determining, an optimal set of wavelet packet atoms, and storing the optimal set of wavelet packet atoms in at least one computer data object,
wherein the determining is via utilizing a Best Basis algorithm; and
f. applying, by the specifically programmed processor, wavelet denoising to the number of wavelet packet atoms in the optimal set;
ii. obtaining the pre-determined ordering of wavelet packet atoms by:
a. projecting, by the specifically programmed processor, the at least one plurality of electrical signal data representative of a brain activity for each 4 second window of the data onto the pre-determined representative set of wavelet packet atoms;
b. storing the projections in at least one computer data object;
c. determining, by the specifically programmed processor, the wire length for every data point in the projection by determining the mean absolute distance of the statistical measure of the projections of different channels from their adjacent channels;
d. storing the wire length data in at least one computer data object; and
e. optionally re-ordering the stored projections, by the specifically programmed computer to minimize a statistical value of the wire length value across each time window, and across all individuals within the plurality of individuals, and across the projections; and;
iii. obtaining the pre-determined set of normalization factors by:
a. determining, by the specifically programmed computer, the mean and standard deviation of the values of the stored projections.

To generate a library of a plurality of pre-determined predictors requires an illustrative library of at least one plurality of electrical signal data representative of a brain activity of a particular brain state. Generation of an illustrative library of at least one plurality of electrical signal data representative of a brain activity of a particular brain state requires obtaining a sufficient collection of electrical signal data representative of a brain activity of a particular brain state (e.g., 100 recordings; 1,000 recording; 10,000 recordings; 100,000 recordings; 1,000,000 recordings, etc.) In general, a recording of 3000 seconds of each event, is sufficient for a robust detection of that brain state event. The larger the number of observations, the more robust the detection is. The electrical signal data representative of a brain activity of a particular brain state can be from a sufficient number of individuals (e.g., 100; 1,000; 10,000; 100,000; 1,000,000, etc.) and be recorded during various (e.g., different in kind, different in intensity, etc.) activities, cognitive tasks and neurological conditions, leading to a variety of brain states.

In some embodiments, the library of a plurality of pre-determined predictors can be tailored to one or more specific goals. For example, if there is a need to emphasize on detection of a specific brain activity event, for example, detection of abnormalities which exist at a certain cortical location occurring before an epileptic seizure occurs, or at an early stage of migraine, then more emphasis should be put on recording during such times. Such emphasis is given by recording from a single subject at times when such event occurs, or recording from multiple subjects at those times. Another example may be recording from subjects that are performing an attention test such as T.O.V.A. test (The TOVA Company, Los Alamitos, CA). Then a recording of a number of subjects performing the same task is obtained, rather than recording from a number of subjects that exhibit a certain brain abnormality such as a certain type of epilepsy. In another example, based on the goal, in some embodiments, a plurality of subjects can be asked to perform a specific cognitive task. Examples of the specific cognitive task include, but are not limited to, memory recall, identification of stimuli, performing an attention task, meditation, learning, watching a movie, observing images, intense concentration during motor operation, and the like.

Deconstructing the at least one plurality of electrical signal data: In some embodiments, the at least one plurality of electrical signal data is recorded over a certain time period. In some embodiments, the at least one plurality of electrical signal data is recorded for up to one hour. In some embodiments, the at least one plurality of electrical signal data is recorded for up to 50 minutes. In some embodiments, the at least one plurality of electrical signal data is recorded for up to 40 minutes. In some embodiments, the at least one plurality of electrical signal data is recorded for up to 30 minutes. In some embodiments, the at least one plurality of electrical signal data is recorded for up to 20 minutes. In some embodiments, the at least one plurality of electrical signal data is recorded for up to 10 minutes.

In some embodiments, the recorded at least one plurality of electrical signal data is deconstructed into a plurality of deconstructed wavelet packet atoms. Each individual deconstructed wavelet packet atom within the plurality of deconstructed wavelet packet atoms corresponds to a brain activity feature ("BAF").

In some embodiments, the exemplary specifically programmed processor of the present invention is programmed deconstruct the at least one plurality of electrical signal data into a plurality of deconstructed wavelet packet atoms, with different mother wavelets, and other orthogonal decompositions such as but not limited to, orthogonal cosine transform and wavelet transform. In some embodiments, the exemplary specifically programmed processor of the present invention is programmed to utilize a particular orthogonal decomposition to minimize the decomposition processing time which is proportional to n log(n) time where n is the number of samples in a window frame.

In some embodiments, the mother wavelet is selected from a wavelet family selected from the group including, but not limited to: Haar, Coiflet Daubehies, and Mayer wavelet families. Other wavelet families suitable for mother wavelets according to some embodiments of the present invention are described in the website located on the world wide web at mathworks.com/help/wavelet/ref/waveletfamilies. In a particular embodiment, optimization of the mother wavelet may also be determined in accordance with Neretti et al. (2002), the entire content of which is incorporated herein by reference.

In some embodiments, the mother wavelet can be chosen by optimization for a given collection of signals. This is a further modification that can be performed when choosing a mother wavelet. See, for example, N. Neretti and N. Intrator An Adaptive approach to wavelets filter design. *IEEE Proceedings on Neural Networks for Signal Processing* pp. 317-326, September 2002; the entire content of which is incorporated herein by reference.

In some embodiments, the exemplary specifically programmed processor of the present invention is programmed to obtained, based on the orthogonal decomposition algorithm, a collection of n dimensional vectors, where each vector represents one BAF.

In some embodiments, the exemplary specifically programmed processor of the present invention is programmed to perform the decomposition to achieve at least one pre-determined goal. For example, the at least one pre-determined goal can be based on identifying a common Best Basis which achieves a particular discrimination at a particular coefficient distribution (an unsupervised/supervised hybrid goal) and which can be commonly utilized for the data analysis with respect to a group of individuals.

In some embodiments, the exemplary specifically programmed processor of the present invention is programmed to determine projections (convolutions) onto the chosen basis functions or some statistics of these projections to generate output interpretive of particular brain activity(ies) associated with particular BAF(s). For example, the exemplary specifically programmed processor of the present invention is programmed to determine particular BAF(s) based on an activity in each such projection. In some embodiments, the exemplary specifically programmed processor of the present invention is programmed to estimate the energy of each projection (e.g., the variance of the signal), a maximal value or other suitable statistical measurement of the orthogonal distribution, such as, but not limited to, a value of the negative entropy.

In some embodiments, the recorded at least one plurality of electrical signal data is deconstructed into a plurality of deconstructed wavelet packet atoms, according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition based on Shannon equation as detailed in section III. Entropy of a vector.

Specifically, the exemplary specifically programmed processor of the present invention identifies a smallest-entropy basis to be utilized in orthogonal decomposition of a particular at least one plurality of electrical signal data. In some embodiments, the exemplary specifically programmed processor of the present invention performs the Shannon entropy analysis on an at least one plurality of electrical signal data to obtain the joint best basis. When considering an at least one plurality of electrical signal data to obtain the joint best basis, the in one embodiment of this patent, it is possible to choose a map M to include additional characteristics which emphasize specific properties of the joint at least one plurality of electrical signal data. For example, if M(1) and M(2) satisfy the definition of the map M being the additive information cost functions, leading to an optimal basis which relies on the sum of both functions. In some embodiments, the exemplary specifically programmed processor of the present invention is programmed to add a new additive cost function which measures a distribution of coefficients at each node in a particular wavelet packet tree to identify the functional M which seeks wavelet packet coefficients with minimal Shannon entropy or with the modified additive optimization function (across the wavelet decomposition) on average across all data observations.

In some embodiments, the recorded at least one plurality of electrical signal data is deconstructed into a plurality of deconstructed wavelet packet atoms, according to another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, the recorded at least one plurality of electrical signal data is deconstructed into a plurality of deconstructed wavelet packet atoms, according to another suitable Best Basis algorithm disclosed in Intrator, N, Neural Computation 5, 443-455 (1993), whose such specific disclosure is incorporated herein by reference.

In some embodiments, the recorded at least one plurality of electrical signal data is deconstructed into a plurality of deconstructed wavelet packet atoms, according to another suitable Best Basis algorithm disclosed in Intrator, N, Neural Computation 4, 98-1-7 (1992), whose such specific disclosure is incorporated herein by reference.

For example, in some embodiments, the exemplary specifically programmed processor of the present invention is programmed to utilize a moving window frame along the time series to obtain different data observations result. In one example, the exemplary specifically programmed processor of the present invention is programmed to utilize a particular window frame and an overlap for the analysis of data segments. In one example, the exemplary specifically programmed processor of the present invention is programmed to utilize a window frame of 4 seconds with an overlap of 75% between consecutive window frames. In some embodiments, the exemplary specifically programmed processor of the present invention is programmed to utilize the window which has a length that is an exponent of 2, so, for example, if sampling rate is 256 Hz, a 4 second window would result in 1024 samples. In another example, if the sampling frequency of 250 Hz, the exemplary specifically programmed processor of the present invention is programmed to utilize the window frame that is a slightly above 4 seconds (e.g., 4.05-4.2). In another example, if the sampling frequency of 496 Hz, the exemplary specifically programmed processor of the present invention is programmed to utilize the window frame that is a slightly above 4 seconds (e.g., 4.05-4.2). In another example, if the sampling frequency of 496 Hz, the exemplary specifically programmed processor of the present invention is programmed to utilize the window frame that is a slightly above 4 seconds (e.g., 4.05-4.2).

In another example, the exemplary specifically programmed processor of the present invention is programmed to utilize a window frame which progresses by 1 second between adjacent frames to obtain vector updates every one second, thus generating a projections matrix of size 121×N (the number of seconds in the data)−3 (due to the first frame of 4 seconds and then each frame progresses by 1 second). In some embodiments, the exemplary specifically programmed processor of the present invention is programmed to rescaling the full matrix to obtain the maximal dynamic range of the visual map of the data.

Determination of the optimal set. In some embodiments, the optimal set of wavelet packet atoms is determined according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition In some embodiments, the optimal set of wavelet packet atoms is determined according to another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, the optimal set of wavelet packet atoms is determined according to another suitable Best Basis algorithm disclosed in Intrator, N, Neural Computation 5, 443-455 (1993), whose such specific disclosure is incorporated herein by reference.

In some embodiments, the optimal set of wavelet packet atoms is determined according to another suitable Best Basis algorithm disclosed in Intrator, N, Neural Computation 4, 98-1-7 (1992), whose such specific disclosure is incorporated herein by reference.

In some embodiments, the number of wavelet packet atoms in the optimal set is reduced by application of the wavelet denoising algorithm disclosed in Donoho D. L., IEEE Transactions on Information Theory, 41(3), 613-627 (1995).

In some embodiments, the number of wavelet packet atoms in the optimal set is reduced by application of an L1 denoising method.

In some embodiments, the number of wavelet packet atoms in the optimal set is reduced by application of an L2 denoising method.

In some embodiments, the number of wavelet packet atoms in the optimal set is reduced by application of a hard threshold method.

Re-ordering the plurality of deconstructed wavelet packet atoms: In some embodiments, the denoised optimal set of wavelet packet atoms is reordered, so that more physiologically correlated BAFs, based on analysis of the total signal data, are visually presented to be geographically/spatially closer.

In some embodiments, the reordering is optional.

In some embodiments, the denoised optimal set of wavelet packet atoms is reordered by the specifically programmed computer performing the steps consisting of:
1. determining the wire length for every data point in the projection by determining either the mean or sum of absolute distance of the statistical measure of the projections of different channels from their adjacent channels;
2. storing the wire length data in at least one computer data object; and
3. re-ordering the stored projections to minimize a value of wither the mean or sum of the wire lengths across the projections, across each 4 second window, and across all individuals within the plurality of individuals.

In some embodiments, the statistical value for the re-ordering is selected from the group consisting of: the mean of the sum of the absolute differences of the wavelet packet atoms, and a mean of the sum of (1−correlation) of the wavelet packet atoms.

Obtaining the pre-determined set of normalization factors: In some embodiments, the set of pre-determined set of normalization factors is obtained by determining the mean and standard deviation of the values of the stored projections.

In some embodiments, the brain activity is represented by the energy of the individual BAF. In some embodiments, the energy is determined based on the variance of the signal. In some embodiments, the energy is the maximal value of the energy of the individual BAF. In some embodiments, the energy is the negative entropy of the energy coefficients of the individual BAF as is Coifman and Wickerhauser.

In some embodiments, the BAFs representation of the subject is used to determine the contribution of each BAF to the total energy of the signal being recorded. For example, the BAFs representation of the subject is used to determine the contribution of each BAF to the total energy of the signal being recorded based, at least in part, on:
1) at least one orthogonal condition utilized for the orthogonal decomposition and/or
2) a summation of orthogonal components utilizing the Parseval's equality which holds for the BAFs representation.

In some embodiments, the BAFs representation of the subject is used to obtain the contribution of each BAF to the total length of a virtual wire that is created from obtaining a wire segmentation of the peaks of BAFs; where the virtual wire identifies at least one communication passage being utilized by isolated brain subsystems of the subject to communicate with each other. In some embodiments, the contribution of each BAF to the total length of the virtual wire measures the smoothness of the brain activity in a different, geographically close BAF.

In some embodiments, the contribution of each BAF to the total energy of the signal and the contribution of each BAF to the total length of each virtual wire that is created from obtaining a wire segmentation of the peaks of BAF activity is used to determine which BAF is being presented in the final BAFs representation. In some embodiments, specific BAFs, which are presented in the BAFs representation of the subject, are those BAFs whose contribution to the variance is suitably high and if their contribution to the total virtual wire length is low.

In some embodiments, the present invention provides a system that is capable of an underlying mental state, an underlying neurological condition, or a combination of an underlying mental state and an underlying neurological condition, in the particular individual. In some embodiments, therefore, the system may be used by a physician.

In some embodiments, the apparatus used to record the electrical activity of the brain of a subject may be worn continuously, and is non-invasive, or unobtrusive. Thus, in some embodiments, the identification of the neurological impairment, or determination of the subject's first mental state may be achieved at an earlier time, or may be achieved more efficiently than other methods, because the subject is monitored in a more natural, or less clinical setting. In some embodiments, the system of the present invention enables an earlier detection, identification, or diagnosis of an individual's mental state and/or neurological condition.

In some embodiments, the present invention provides a specifically programmed computer system including:
a. at least one specialized computer machine comprising:
i. a non-transient memory, electronically storing particular computer executable program code; and
ii. at least one computer processor which, when executing the particular program code, becomes a specifically programmed computer processor configured to perform at least the following operations:
1. obtaining, in real-time, by a specifically programmed processor, electrical signal data representative of brain activity of a particular individual;
2. processing, in real-time the electrical signal data representative of brain activity of a particular individual based upon an individual pre-determined predictor associated with a particular brain state, selected from a library of predictors containing a plurality of pre-determined predictors, wherein each individual pre-determined predictor is associated with a unique brain state,
wherein the pre-determined predictor associated with a particular brain state comprises:
i. a pre-determined mother wavelet,
ii. a pre-determined representative set of wavelet packet atoms,
iii. a pre-determined ordering of wavelet packet atoms, created from the pre-determined mother wavelet, and
iv. a pre-determined set of normalization factors,
wherein the processing comprises:
i. causing, by the specifically programmed processor, the electrical signal data to be deconstructed into a plurality of pre-determined deconstructed wavelet packet atoms, utilizing the pre-determined representative set of wavelet packet atoms,
wherein time windows of the electrical signal data are projected onto the pre-determined representative set of wavelet packet atoms
wherein the projection is via convolution or inner product, and
wherein each pre-determined representative wavelet packet atom corresponds to a particular pre-determined brain activity feature from a library of a plurality of pre-determined brain activity features;
ii. storing the plurality of pre-determined deconstructed wavelet packet atoms in at least one computer data object;
iii. causing, by the specifically programmed processor, the stored plurality of pre-determined deconstructed wavelet packet atoms to be re-ordered within the computer data object, based on utilizing a pre-determined order;
iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and
3. outputting, a visual indication of at least one personalized mental state of the particular individual, at least one personalized neurological condition of the particular individual, or both, based on the processing,
wherein an individual pre-determined predictor associated with a particular brain state within the plurality of pre-determined predictors is generated by the steps consisting of:
ii. obtaining the pre-determined representative set of wavelet packet atoms by:
1. obtaining from a plurality of individuals, by the specifically programmed processor, at least one plurality of electrical signal data representative of a brain activity of a particular brain state;
2. selecting a mother wavelet from a plurality of mother wavelets, wherein mother wavelet is selected from an wavelet family selected from the group consisting of: Haar, Coiflet Daubehies, and Mayer wavelet families, optimization of the mother wavelet may also be determined in accordance with Neretti et al. (2002), the entire content of which is incorporated herein by reference;

3. causing, by the specifically programmed processor, the at least one plurality electrical signal data to be deconstructed into a plurality of wavelet packet atoms, using the selected mother wavelet;

4. storing the plurality of wavelet packet atoms in at least one computer data object;

5. determining, an optimal set of wavelet packet atoms using the pre-determined mother wavelet, and storing the optimal set of wavelet packet atoms in at least one computer data object, wherein the determining is via utilizing a Best Basis algorithm; and 6. applying, by the specifically programmed processor, wavelet denoising to the number of wavelet packet atoms in the optimal set;

ii. obtaining the pre-determined ordering of wavelet packet atoms by:

1. projecting, by the specifically programmed processor, the at least one plurality of electrical signal data representative of a brain activity for each 4 second window of the data onto the pre-determined representative set of wavelet packet atoms;

2. storing the projections in at least one computer data object;

3. determining, by the specifically programmed processor, the wire length for every data point in the projection by determining the mean absolute distance of the statistical measure of the projections of different channels from their adjacent channels;

4. storing the wire length data in at least one computer data object; and 5. re-ordering the stored projections, by the specifically programmed computer to minimize a statistical value of the wire length value across each time window, and across all individuals within the plurality of individuals, and across the projections; and iii. obtaining the pre-determined set of normalization factors by:

1. determining, by the specifically programmed computer, the mean and standard deviation of the values of the stored projections.

In one embodiment, the specifically programmed computer system further includes:

a. at least one specialized computer machine including:
   i. a non-transient memory, electronically storing particular computer executable program code; and
   ii. at least one computer processor which, when executing the particular program code, becomes a specifically programmed computer processor configured to perform at least the following operations:
      1. obtaining, in real-time, by a specifically programmed processor, data representative of (i) at least one physiological parameter of the individual, selected from the group consisting of: heart rate, blood oxygen and/or carbon dioxide levels, body temperature, respiration rate, skin temperature, skin conductivity, and movement, and (ii) at least one environmental parameter; and
      2. determining a relationship between the obtained data and the visual indication of at least one personalized mental state of the particular individual, at least one personalized neurological condition of the particular individual, or both.

Methods of Inducing Changes in the Mental State, the Neurological Condition, or Both, in a Subject In some embodiments, a system is presented, comprising:
a. an apparatus configured to apply at least one stimulus to a subject;
b. an apparatus configured to record the electrical activity of the subject's brain and determine the mental state, neurological condition, or both, of the subject, and to record the response the subject has to the at least one stimulus.

In some embodiments, the system further comprises a neural feedback mechanism that is configured to:
a. determine the stimulus that the subject is capable of responding to;
b. alter the nature, magnitude, or duration of the response; or
c. both a and b.

In some embodiments, the response may be a cognitive response. Alternatively, in some embodiments, the response may be an emotional response.

In some embodiments, the system is portable. In some embodiments, the system is configured to provide a real-time interpretation of the activity of the subject's brain.

In some embodiments, the at least one stimulus is selected from the group consisting of: an auditory stimulus, a tactile stimulus, an olfactory stimulus, a visual stimulus, or any combination thereof. Any device configured to provide a stimulus may be used. Examples include, but are not limited to, a speaker, a toy, a game, a projector, a computer screen, and the like.

In some embodiments, the device configured to provide the at least one stimulus is operated remotely from the subject.

In some embodiments, the subject may be monitored remotely, such as, for example, by a caregiver, or a family member.

For example, by way of illustration, the device configured to provide a stimulus may be a bi-directionally operated toy, wherein the toy is configured to attract the attention of an infant. The toy may be manipulated remotely (such as, for example, via Bluetooth), to move and/or change colors. The colors may represent the emotional state of the infant and the movement may represent specific cognitive or emotional state change.

In some embodiments, the device configured to provide the at least one stimulus is the interactive toy disclosed in U.S. Pat. No. 6,773,344.

In some embodiments, the system is further configured to monitor and record the subject's response to the at least one stimulus over time, and determine if the response to the at least one stimulus changes over time. In some embodiments, the system is configured to issue an alert if the response to the at least one stimulus changes.

In some embodiments, the subject is an infant. Without intending to be limited to any particular theory, in the first few months of a child's development there are several key brain developments, which influence the child for life. These developments include, for example, but are not limited to:

1. Development of motor and other cortical activity, such as, for example, catching an object by closing the fist, eye movement control and two hands coordination;
2. Development of sensory perception;
3. The co-processing of sensor inputs, such as, for example, visually seeing a word spoken, and hearing the word spoken;
4. Development of decision abilities, such as, for example which toy to look at, which toy to catch, and the like; and/or
5. Development of speech and sound preprocessing.

The developments listed above can be influenced by a variety of factors, including, for example, the subject's health, the environment, nutrition, familial interaction, enrichment, play, stimulation, sleep, neurological disorders, and the like.

By way of illustration, if an infant is not exposed to faces at an early age (or is deliberately not looking at faces), the facial expression analysis will not develop and consequently, the infant may lose to a certain degree the ability to understand facial expressions, one of the key tools of social communication, this can later affect social skills in general, as the developing infant and later child, will not be looking at the face of the other person during social interaction, causing social stress to the second person and consequently reducing social interaction.

Additionally, if the infant is not watching people uttering phonemes and then words during the development of speech recognition and production, the infant's ability to produce accurate sounds may be affected, to a point where the utterance is illegible.

The earlier the detection of a change in the developmental path the easier it is to bring back the development onto the right path with minimal or no damage.

Without intending to be limited to any particular theory, the methods and systems according to some embodiments of the present invention are able to (i) detect abnormalities in the development of an infant, by obtaining a visual representation of the mental state of the infant, which is then used to identify an underlying mental state, an underlying neurological condition, or a combination of an underlying mental state and an underlying neurological condition in the infant; (ii) apply stimuli to the infant, using a stimulating apparatus which creates different stimuli attempting to detect the infant's attention and sustained attention to each stimulus, and the response time to each stimulus; (iii) obtaining a visual representation of the mental state of the infant following the stimuli, which is then used to quantify the infant's response to the stimuli, and (iv) a neural feedback mechanism, which is used to treat the abnormalities in the development of an infant.

In some embodiments, the infant may be rewarded, or encouraged to elicit an improved, or normal developmental task.

In some embodiments, an infant is attached to an EEG monitor while auditory stimulation is played in the background. The infant is free to move around and play with toys. A certain tonal music is being repeated between other pieces of music. The EEG data recording and processing system is controlling the music stimulation as well (from the cloud) by streaming the music to the music player. The specific pattern of response to the specific music piece is collected and analyzed together. This enables to detect whether there are similarities in the response pattern of the BAF (described in detail in main technology patent).

In some embodiments, as the different BAF channels are ordered based on their correlation (on a large data set of recordings), similarity of sub parts (different small groups of consecutive BAF channels) from the full BAF vector is sought. By performing clustering of a certain collection of BAF channels across the entire recording, it is possible to determine whether responses to the music actually form or are a part of the same cluster. Furthermore, it is possible to determine whether the early response is different than response to the same music piece after few repetitions, indicating potential familiarity or habituation to the specific music piece. By performing the same analysis many times and on different pieces of music, it becomes possible to determine whether there is a similar pattern of changing response to a music piece that was played several times, whether the response is the same to "complex" music pieces vs. "simple" ones and whether this changes as the infant develops. By repeating the same music piece few hours later or few days later, it is then possible to examine the short and long term memory consolidation abilities of the infant as a function of age, see the degree of complexity of the music pieces to which the infant responds to in a similar manner and determine the babies memory, attention and comparison abilities. Furthermore, by changing one or more notes in the music piece it is possible to determine whether the infant notices the change, by noticing a difference in brain activity response as is measured with the BAFs.

Different complexity of musical and other stimuli can be provided to babies at different ages. Using said inference, one may determine at what age an infant starts responding to the different stimuli and this can be used to quantify infant's development. For example, it is possible to determine whether an infant responds to faces, to familiar faces, to facial expressions, to faces correlated with sounds and so forth.

In some embodiments, the mood of the subject (such as, for example, a developing infant) may be inferred. For example, by way of illustration, in some embodiments, mood is inferred from channels related to stress and happiness in the BAF representation. In some embodiments, channels related to stress are 1-4 negatively correlated and 34-37, 113-114, 119-121 positively correlated. In some embodiment, increased activity in those channels may indicate stress, anxiety or pain suffering. Caregiver intervention may differentiate between these possibilities.

In some embodiments, a mood disorder may be detected. For example, by way of illustration, in some embodiments, channels correlated with positive mood are 34-38 and 113-114 and another set is 119-121. In some embodiments, the first is more related to positive mood as a result of external stimuli, such as seeing a happy movie, while the latter is more related to an inner feeling such as a personal achievement that causes happiness. Lack of activity in these channels may indicate depression.

In some embodiments, attention disorder may be correlated with lack of attention to the stimuli, in this case, there will be times where the same stimuli will cause the desired response, for example indication of familiarity with the stimulation, while in others, the infant may be occupied by other distractors and the same stimulus will not produce the same response.

In some embodiments, OCD may be indicated by some repeated brain activity which can be inferred via the said inference mechanism, but may not be found to be correlated to external stimuli, but rather to internal brain activity.

In some embodiments, memory consolidation or lack thereof as measured by lack of response to familiar stimuli may be an indication to attention deficiencies or other brain developmental disorders which can be further discerned by a developmental expert. Early detection and intervention is key to quickly alleviating the problem.

In some embodiments, response to familiar faces or to facial expression or lack thereof may be an indication of a behavior that is on the autistic spectrum.

In some embodiments, the setup of producing different stimuli can be used to enhance and improve brain development. This can be achieved by providing more often stimuli that the infant seems to have difficulty in recognizing, thus developing the infant's ability to analyze and recognize such stimuli. Also, positive reinforcement (by words, sound, or color) can increase infant's attention span and motivate the infant to be attentive and respond.

In some embodiments, methods and systems described herein can be used to enhance sleep quality by accelerating falling asleep, reducing sleep apnea, and expanding deep sleep length relative to that characteristic of light sleep cycles.

In some embodiments, the system provides cognitive and emotional stimulation and feedback. In some embodiments, the system provides statistics to caregivers about the brain states of the subject (such as, for example, the percentage of time the subject is focused, happy, stressed, conscious, etc). In some embodiments, the system provides a tool to teach a child to control his different emotions, and different cognitive actions.

In some embodiments, the system is further configured to assess the subject's cognitive, development abilities, or both. For example, in the case where the subject is an infant, the system is configured to monitor the development of the subject, and determine when, and if the infant achieves certain developmental milestones.

In another example, where the subject is an individual in a minimal conscious state, the system is configured to monitor the brain activity of the subject and determine if the subject reaches a higher level of consciousness.

In some embodiments, the system is configured to monitor and encourage the creation of healthy habits (such as, but not limited to sleeping, playing, and eating). By way of illustration the system can monitor times when the subject is asleep, or the quality of sleep, sleep depth, the time taken to fall asleep, the time taken to wake up, or any combination thereof. The system utilizes the recorded parameters, and can provide the subject (e.g. an infant) with auditory feedback that encourage relaxation, and accelerate sleep. In additional embodiments, during sleep, the music can be changed to enable deeper and better relaxation.

In some embodiments, the system can monitor stress and relaxation levels. In some embodiments, the system can issue an alert when the subject (e.g. an infant) feels uncomfortable or stressed, and provides self-adjusted relaxing sounds, vibrates or displayed pictures and lights.

In some embodiments, the system monitors self-quieting activities by an infant, or, how frequently, or quickly the infant is capable of calming itself, and assisting the infant in the relaxation process by playing self-adjusted relaxing sounds, vibrations or displaying pictures and lights.

In some embodiments, the system is configured to monitor a subject's (e.g. an infant's) learning capacities, or the ability of the subject to learn new categories. In some embodiments, the system produces rows of stimuli that relate in the same category, and attach to the row a single stimuli from an unrelated category (possible category types: musical stimuli from the same category, semantical stimuli from the same category, subject related categories such colors, animals, words and numbers, or any other type of category). The system analyzes the subject's reaction to the unrelated stimulus by measuring attention levels, reaction time and the number of times stimulus should be presented in order to facilitate learning of the category. The system provides a reward if the subject succeeds to discriminate the unrelated stimulus. The category may become more and more complex as the subject demonstrates the ability discriminate simple differences.

For example, the system may monitor an infant's reaction toward human vs. non-human sounds. In some embodiments, the system produces sounds of human singing and humming, and the sounds of its correlated tonal melodies. The system analyzes the levels of excitement and attention. If the infant does not prefer the human voice, the system binds the human singing and humming sounds to more engaging stimuli, that is self-adjusted to the individual infant's preference—for example—flickering light that are presented on a display.

In another example, the system may monitor reaction toward social stimuli, such as, for example, the infant's own name, faces, or laughter. In some embodiments, the system produces the infant's name by both the caregiver voice and a stranger's voice. The system analyzes the levels of excitement and the infant's reaction time. If the infant does not react, the system binds the name to more engaging stimuli, that is self-adjusted to the individual infant's preference—for example—flickering light that are presented on a display.

In another example, the system can monitor learning capacities, such as, for example, response toward a familiar stimulation vs. unfamiliar, or the ability to inhibit and dis-inhibit information. In some embodiments, the system produces a long and persistent stimulus that changes after amount of time. The system analyzes the infant's reaction times, attention levels, and the ability to inhibit and dis-inhibit the stimulus. If the infant fails to inhibit the stimulus it would fade out gradually, and the process will repeat itself. If the infant fails to dis inhibit it a new stimulus will be performed and for a shorter duration.

In some embodiments, the system can monitor the learning of language prosody. In some embodiments, the system produces sounds with different acoustic intonation that can differ in pitch, height, range/variability and melodic contour. The system analyzes the infant's duration to react, level of attention, and time to disengage. If the infant reaction is slow, or not attentive to the sounds the system will provide more instance intonation.

In some embodiments, the system can monitor learning capacities; quality of engagement with a complex stimulus as a function of its complexity. In some embodiments, the system produces both simple and complex musical and visual stimuli, and analyze the infant's changes in excitement and attention levels, the duration to engage with each stimulus, and the number of times each complex stimulus should be presented until it became trivial to the infant. The system can provide more and more complex stimuli, until the infant will no longer be attentive. Rows of stimuli can start with more complex once as the infant sharpen his discrimination skills.

In some embodiments, the system is employed in a method comprising:
  a. recording electrical or magnetic brain activity using at least one modality such as EEG, MEG, or depth electrodes;
  b. obtaining Brain Activity Features (BAF) in an unsupervised or semi-supervised manner. This relies on finding useful signal decompositions using decomposition methods like harmonic analysis, which are more refined methods to principal or independent components analysis.
c. obtaining a predictor for a specific brain state using a machine learning algorithm from the given set of observations as represented by the said BAF.
d. the predictor can then be found from the clustered brain states using machine learning algorithms.
e. from the clusters of step 3, it is possible to obtain temporal dependency between cluster memberships, so that each cluster can be labeled by a letter. Then, "words" which are composed of these letters can be obtained, and segmentation as well as text analysis techniques can be applied to the new collection of letters.

In some embodiments, step 3 can be replaced by a clustering which reduces the dimensionality of the BAF into a number of brain states.

In some embodiments, the present invention provides a method, wherein the method induces a change in the mental state, neurological condition, or both, of a subject from a first mental state, first neurological condition, or both, to a second mental state, a second neurological condition, or both, the method comprising:
a. obtaining a first visual indication of a first mental state, first neurological condition, or both, of a subject;
b. applying at least one first stimulus to the subject and obtaining a second visual indication of a second mental state, second neurological condition, or both, of the subject;
c. comparing the first visual indication of a first mental state, first neurological condition, or both, of the subject to the second visual indication of a second mental state, second neurological condition, or both, of the subject;
d. based on the comparison, determining if the second mental state, second neurological condition, or both, of the subject is different from the first mental state first neurological condition, or both, and, if the second mental state, second neurological condition, or both, of the subject is not different from the first mental state, first neurological condition, or both;
e. iteratively
  i. applying at least one subsequent stimulus to the subject,
    wherein each at least one subsequent stimulus is different from the preceding at least one stimulus;
  ii. obtaining a subsequent visual indication of a mental state, neurological condition, or both of the subject;
  iii. comparing the first visual indication of a first mental state, first neurological condition, or both, of the subject to the subsequent visual indication of a mental state, neurological condition, or both, of the subject;
  iv. based on the comparison, determining if the mental state, neurological condition, or both of the subject is different from the first mental state, first neurological condition, or both,
    wherein steps i to iv are performed until the mental state, neurological condition, or both, is different from the first mental state, first neurological condition, or both.

In some embodiments, the present invention provides a method,
wherein the method induces a change in the mental state, neurological condition, or both of a subject from a first mental state, first neurological condition, or both, to a desired mental state, desired neurological condition, or both, the method comprising:
a. obtaining a first visual indication of a first mental state, first neurological condition, or both, of a subject;
b. applying at least one first stimulus to the subject and obtaining a second visual indication of a second mental state, second neurological condition, or both, of the subject;
c. determining if the second visual indication of a second mental state, second neurological condition, or both, of the subject is indicative of the desired mental state, second neurological condition, or both, and if not;
d. iteratively,
  i. applying at least one subsequent stimulus to the subject, wherein each at least one subsequent stimulus is different from the preceding at least one stimulus;
  ii. obtaining a subsequent visual indication of a mental state, neurological condition, or both, of the subject;
  iii. determining if the subsequent visual indication of the mental state, neurological condition, or both, of the subject is indicative of the desired mental state, desired neurological condition, or both,
    wherein steps i to iii are performed until the desired mental state, desired neurological condition, or both, is obtained.

In some embodiments, the present invention provides a method,
wherein the method induces a change in the mental state, neurological condition, or both, of a subject from a first mental state, first neurological condition, or both, to a desired mental state, desired neurological condition, or both, the method comprising:
a. obtaining a first visual indication of a first mental state, first neurological condition, or both of a subject;
b. applying at least one first stimulus to the subject and obtaining a second visual indication of a second mental state, second neurological condition, or both of the subject;
c. determining if the second visual indication of a second mental state, second neurological condition, or both of the subject is indicative of the desired mental state, desired neurological condition, or both, and if not;
d. iteratively,
  i. comparing the first visual indication of a first mental state, first neurological condition, or both of the subject to the second visual indication of a second mental state, second neurological condition, or both of the subject;
  ii. based on the comparison, selecting a subsequent stimulus and applying the selected subsequent stimulus to the subject,
    wherein each at least one subsequent selected stimulus is different from the preceding at least one stimulus;
  iii. obtaining a subsequent visual indication of a mental state, neurological condition, or both of the subject;
  iv. determining if the subsequent visual indication of the mental state, neurological condition, or both of the subject is indicative of the desired mental state, desired neurological condition, or both, wherein steps i to iv are performed until the desired mental state, desired neurological condition, or both, is obtained.

In some embodiments, the present invention provides a method,
wherein the method provides a reward if a subject elicits a desired mental state, desired neurological condition, or both, in response to an at least one first stimulus, the method comprising:
a. obtaining a first visual indication of a first mental state, first neurological condition, or both of a subject;
b. applying at least one first stimulus to the subject and obtaining a second visual indication of a second mental state, second neurological condition, or both of the subject;
c. determining if the second visual indication of a second mental state, second neurological condition, or both of the subject is indicative of the desired mental state, desired neurological condition, or both, and providing a reward;
d. if, however, the second visual indication of a second mental state, second neurological condition, or both of the subject is not indicative of the desired mental state, desired neurological condition, or both;
e. iteratively,
i. comparing the first visual indication of a first mental state, first neurological condition, or both of the subject to the second visual indication of a second mental state, second neurological condition, or both of the subject;
ii. based on the comparison, selecting a subsequent stimulus and applying the selected subsequent stimulus to the subject,
wherein each at least one subsequent selected stimulus is different from the preceding at least one stimulus;
iii. obtaining a subsequent visual indication of a mental state, neurological condition, or both of the subject;
iv. determining if the subsequent visual indication of the mental state, neurological condition, or both of the subject is indicative of the desired mental state, desired neurological condition, or both,
wherein steps i to iv are performed until the desired mental state, desired neurological condition, or both, is obtained.

In some embodiments, the present invention provides a method,
wherein the method identifies a stimulus that a subject is capable of responding to, the method comprising:
a. obtaining a first visual indication of a first mental state, a first neurological condition, or both, of a subject;
b. applying at least one first stimulus to the subject and obtaining a second visual indication of a second mental state, a second neurological condition, or both, of the subject;
c. comparing the first visual indication of the first mental state, the first neurological condition, or both, of the subject to the second visual indication of a second mental state, second neurological condition, or both, of the subject;
d. based on the comparison, determining
i. if the second mental state, second neurological condition, or both, of the subject is different from the first mental state, the first neurological condition, or both, and, if the second mental state, the second neurological condition, or both, of the subject is different from the first mental state, first neurological condition, or both,
ii. determining if the difference between the second mental state, the second neurological condition, or both, and the first mental state, the first neurological condition, or both, is a coherent response to the at least one first stimulus;
and if the difference between the second mental state, the second neurological condition, or both, and the first mental state, the first neurological condition, or both, is not a coherent response to the at least one first stimulus;
e. iteratively
i. applying at least one subsequent stimulus to the subject,
wherein each at least one subsequent stimulus is different from the preceding at least one stimulus;
ii. obtaining a subsequent visual indication of a mental state, neurological condition, or both of the subject;
iii. comparing the first visual indication of the first mental state, the first neurological condition, or both, of the subject to the subsequent visual indication of a mental state, neurological condition, or both, of the subject;
iv. based on the comparison, determining if the subsequent mental state, neurological condition, or both of the subject is
1. different from the first mental state, the first neurological condition, or both, and
2. the difference between the second mental state, the second neurological condition, or both, and the first mental state first neurological condition, or both, is a coherent response to the at least one first stimulus,
wherein steps i to iv are performed until the subsequent mental state, the neurological condition, or both, of the subject is different from the first mental state, first neurological condition, or both, and the difference between the second mental state, the second neurological condition, or both, and the first mental state, the first neurological condition, or both, is a coherent response to the at least one first stimulus.

In some embodiments, a temporal structure probabilistic model is applied to the BAF's to determine the correlation between the at least one stimulus applied and the observed brain activity. In some embodiments, a strong correlation indicates a coherent response to the at least one stimulus.

In some embodiments, the degree of response ("RtS") is used to identify the at least one stimulus that the subject is capable of responding to.

In some embodiments, the method further comprises the step of issuing an alert if the at least one first stimulus causes a change in the subject's mental state, neurological condition, or both.

In some embodiments, the method further comprises the step of issuing an alert if the at least one second stimulus causes a change in the subject's mental state, neurological condition, or both.

In some embodiments, the at least one first stimulus is selected from the group consisting of: an auditory stimulus, a tactile stimulus, an olfactory stimulus, a visual stimulus, or any combination thereof.

In some embodiments, the at least one subsequent stimulus is selected from the group consisting of: an auditory stimulus, a tactile stimulus, an olfactory stimulus, a visual stimulus, or any combination thereof.

In some embodiments, the at least one subsequent stimulus is different from the at least one first stimulus.

In some embodiments, the methods and systems according to some embodiments of the present invention are able to identify stimuli that a subject that is in a minimally conscious state (MCS) can respond to.

In some embodiments, RtS can indicate the type of stimuli that a person that is in a Minimal Conscious State (MCS) responds to. For example, it can help determine whether the person responds in a consistent way to visual stimuli, auditory stimuli, other sensory stimuli, commands, and the like.

In some embodiments, the identification of stimuli that the subject can respond to can optimize medical intervention that aims to increase response to various stimuli. In the case of a subject in MCS, for example, a physician, or care giver, can look at the entropy of the alphabet and produce a single number which determines the total entropy of the alphabet (just based on letters or also based on more sophisticated grammatical rules that are inferred and length of words that are inferred.

In one specific embodiment, the said alphabet can be used to create music. In some embodiments, the music can enable a MCS subject to produce some means of communication and to obtain neural feedback on the subject's brain activity.

In some embodiments, different letters can produce different musical notes with different musical instruments or can be used to change tempo and other musical parameters. The result would be a melody that is produced from an MCS subject's brain and can provide a means of communication. For example, by way of illustration, an MCS subject may learn to operate external devices once a control on the production of these letters is achieved.

Reference is now made to the following examples, which together with the above descriptions illustrate some embodiments of the invention in a non-limiting fashion.

ILLUSTRATIVE EXAMPLES IN ACCORDANCE WITH AT LEAST SOME EMBODIMENTS DESCRIBED HEREIN

Example 1: Optimizing DBS for Parkinson's Patients

FIG. 1 depicts brain activity as described in WO 2016/132228 and U.S. Patent Application Publication No. 2017/0347906, the entire content of each of which is incorporated herein by reference. The horizontal red lines are an indication of the activity of the DBS. At some point, the DBS is turned off (black arrow), and as shown in FIG. 1, brain activity is significantly reduced when DBS is turned off. It is important to study brain activity during a specific task which is challenging to the subject and is strongly affected by the disorder such as Parkinson's. In the present example, the challenging task is to stand on a balance board. Standing on a balance board requires quick communication between the two brain hemispheres and quick balance in each hemisphere. For healthy subjects, this task activates cognitive region A which includes features from 20 to 60.

Figure 2:
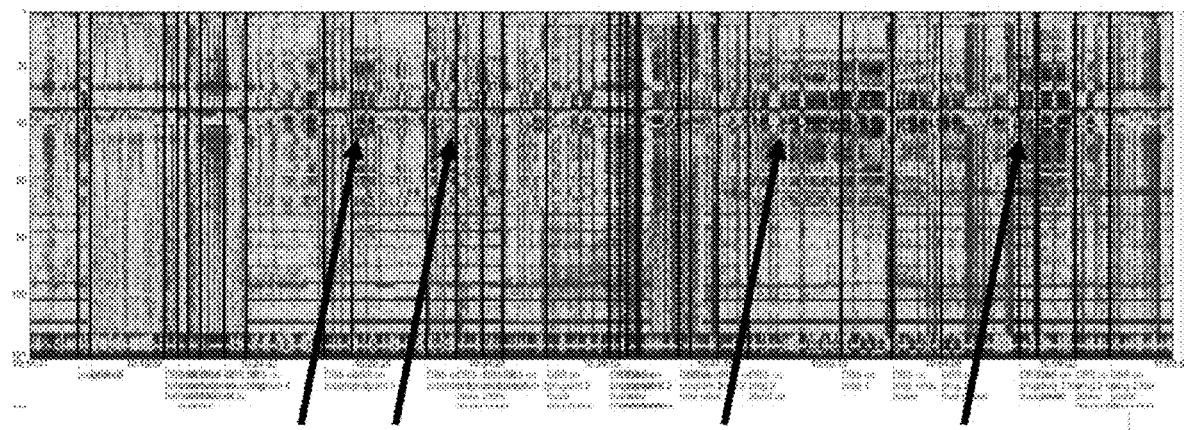
FIG. 2 shows a screenshot of an example of a representation of a recording of brain activity of a Parkinson's patient during the same task performed with four different DBS parameters. An arrow points each such activity. The second set of parameters demonstrates that the activity in the region between 20 to 60 is increased (less blue).

FIG. 2 shows the effect of different DBS stimulation parameters on the brain activity as is measured as described in WO 2016/132228 and U.S. Patent Application Publication No. 2017/0347906, the entire content of each of which is incorporated herein by reference. The subject is performing the same task: standing on a balance board four times, each with a different DBS parameter set. Comparison of the activities indicates the parameter set that produces a more desired brain activity, which, in this case, should contain more activity (yellow or red) in features 20 to 60. As shown in FIG. 2, the second set of parameters produces more brain activity.

Example 2: Optimizing Stimulation Location, Strength, and Duration to Produce Increased Activity in a Desired Region In a particular embodiment, stimulation location, strength, and duration of a transcranial direct current stimulation (tDCS) device can be optimized to produce increased activity in the 20 to 60 region (described in Example 1), or in the "executive" region of 35 to 39, a region which is less active for comatose patients. If the goal is to reduce stress, then other BAFs in the 60 to 121 may be used for the optimization.

The same optimization can be done to transcranial alternating current stimulation (tACS), as well as magnetic and ultrasound stimulation, but in these cases, the specific pattern of stimulation, frequency, and morphology can also be optimized.

It is also possible to optimize the required activity of the subject during the stimulation to produce optimal stimulation effect. A person can perform a passive operation such as watching a movie or listening to music, in which case, the specific music, verbal stimulation or a movie type can be optimized (emotional, cognitively challenging, etc). In another embodiment, the subject may be required to perform an active cognitive or motor task during stimulation to activate the region that is being stimulated.

Database of optimal stimuli can be collected to serve as a baseline for stimuli of new patients and thus, continue to grow the database as new optimal parameters are found. Big data analytics tools can, furthermore, be used to minimize the search for optimal parameters based on the profile of the subject and brain activity response to different stimuli.

In a different embodiment, the optimal time when to apply a brain stimulation can also be found. Application of stimulation during different stages of sleep can be pursued, and the effect of the stimulation can guide when it is optimal to stimulate. Similarly, application of stimulation may be performed during the waking state of a subject that is conscious or with minimal consciousness and the effect of the stimulation can guide when it is optimal to stimulate.

In one embodiment, stimulation of the vagus nerve at different locations (on the neck, invasively around the nerve or in the ear) can be optimized.

In a different embodiment, stimulation of the spinal cord at different locations can be optimized, for reduced pain or improved brain activity.

In one embodiment, the sleep quality, the level of anxiety, the attention level and cognitive activity can be used to optimize the stimulation parameters.

FIG. 3 indicates a brain state that is characterized by excess (brown/red) activity in multiple BAFs. Such excessive activity also lasts continuously for at least several minutes. Such activity is not indicative of a healthy state and may be associated with accelerated cell death due to lack of sufficient oxygen to support the excessive activity. In one embodiment, brain stimulation of different types can be applied to reduce the amount of such excessive activity.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

The invention claimed is:

1. A system comprising:
   a stimulation device for administering at least one stimulus;
      wherein the at least one stimulus is configured to modulate brain electrical activity of an individual while the individual is performing a particular activity;
   an apparatus configured to be worn on a head of the individual and comprising at least one sensor to detect:
      i. the particular activity performed by the individual;
      ii. brain electrical activity of the individual associated with the particular activity;
         wherein the brain electrical activity of the individual is detected while the individual is performing the particular activity;
         wherein the at least one stimulus promotes the ability of the individual to perform the particular activity; and
   a specifically programmed computer system coupled to the stimulation device and the apparatus;
      wherein the specifically programmed computer system comprises:
         i. a non-transient memory, electronically storing particular computer executable program code; and
         ii. at least one computer processor which, when executing the particular program code, becomes a specifically programmed computer processor configured to perform at least the following operations:
            projecting, in real time, the detected brain electrical activity of the individual while the individual is performing the particular activity onto a denoised optimal set of wavelet packet atoms to obtain a particular set of projections of the individual;
            assessing, in real time, the brain electrical activity of the individual while the individual is performing the particular activity relative to a representative brain electrical activity of a plurality of individuals performing the particular activity by applying at least one machine learning algorithm to the particular set of projections of the individual;
               wherein the at least one machine learning algorithm is trained by the plurality of individuals performing the particular activity and the brain electrical activity collected from the plurality of individuals associated with performing the particular activity;
            determining a relationship between:
               i. the particular activity performed by the individual,
               ii. the detected brain electrical activity of the individual associated with the particular activity,
               iii. the assessing, in real time, of the brain electrical activity of the individual associated with the particular activity relative to the representative brain electrical activity of the plurality of individuals performing the particular activity by using the at least one machine learning algorithm, and
               iv. the at least one stimulus; and
            causing to adjust, based on the relationship, the at least one stimulus from the stimulation device to promote the ability of the individual to perform the particular activity.

2. The system of claim 1, further comprising at least one apparatus configured to administer the at least one stimulus, wherein the at least one apparatus is an invasive deep brain stimulation device or a non-invasive brain stimulator.

3. The system of claim 1, wherein promoting the ability of the individual to perform the activity comprises enhancing the ability of the individual to perform the activity to at least partially achieve that of a pre-determined level of ability with respect to the particular activity.

4. The system of claim 1, wherein the individual has a disease or disorder that impairs the individual's ability to perform the particular activity.

5. The system of claim 4, wherein the disease or disorder comprises at least one of Parkinson's disease, tremors, motor dysfunction, dyskinesia, gate freeze, epilepsy, migraine headaches, pain, anxiety, depression, mood swings, attention deficit disorders, sleep disorders, or cognitive decline disorders.

6. A method comprising:
   detecting:
      i. a particular activity performed by an individual, and
      ii. brain electrical activity of the individual associated with the particular activity;
   administering at least one stimulus to modulate brain electrical activity of an individual while the individual is performing the particular activity;
      wherein the at least one stimulus promotes the ability of the individual to perform the particular activity;
   detecting brain electrical activity of the individual while the individual is performing the particular activity;
   projecting, in real time, the detected brain electrical activity of the individual while the individual is performing the particular activity onto a denoised optimal set of wavelet packet atoms to obtain a particular set of projections of the individual;
   assessing, in real time, the brain electrical activity of the individual while the individual is performing the particular activity relative to a representative brain electrical activity of a plurality of individuals performing the particular activity by applying at least one machine learning algorithm to the particular set of projections of the individual;
      wherein the at least one machine learning algorithm is trained by the plurality of individuals performing the particular activity and the brain electrical activity collected from the plurality of individuals associated with performing the particular activity;

determining a relationship between:
i. the particular activity performed by the individual,
ii. the detected brain electrical activity of the individual associated with the particular activity,
iii. the assessing, in real time, of the brain electrical activity of the individual associated with the particular activity relative to the representative brain electrical activity of the plurality of individuals performing the particular activity by using the at least one machine learning algorithm, and
iv. the at least one stimulus; and adjusting, based on the relationship, the at least one stimulus to promote the ability of the individual to perform the particular activity.

7. The method of claim 6, wherein the administering the at least one stimulus is performed by at least one apparatus, wherein the at least one apparatus is an invasive deep brain stimulation device or a non-invasive brain stimulator.

8. The method of claim 6, wherein promoting the ability of the individual to perform the particular activity comprises enhancing the ability of the individual to perform the activity to at least partially achieve that of the pre-determined level of ability with respect to the particular activity.

9. The method of claim 6, wherein the individual has a disease or disorder that impairs the individual's ability to perform the particular activity.

10. The method of claim 9, wherein the disease or disorder comprises at least one of Parkinson's disease, tremors, motor dysfunction, dyskinesia, gate freeze, epilepsy, migraine headaches, pain, anxiety, depression, mood swings, attention deficit disorders, sleep disorders, or cognitive decline disorders.

11. The method of claim 6, wherein the individual has Parkinson's disease; and wherein the particular activity is walking; and wherein the adjusting, based on the relationship, at least one stimulus promotes the ability of the individual having Parkinson's disease to walk.

12. The method of claim 6, wherein the individual has gate freeze, and wherein the at least one stimulus promotes the ability of the individual to resume walking.

13. The method of claim 6, wherein the individual has a sleep disorder; and wherein the particular activity is sleeping; and wherein the adjusting, based on the relationship, the at least one stimulus promotes the ability of the individual having the sleep disorder to sleep.

14. The method of claim 6, wherein the individual has a cognitive disorder; and wherein the particular activity is an activity that leads to a cognitive challenge in the individual; and wherein the adjusting, based on the relationship, the at least one stimulus promotes the ability of the individual with the cognitive disorder to meet the cognitive challenge.

15. The method of claim 6, wherein the individual has an anxiety disorder; and wherein the particular activity is an anxiety provoking activity that provokes anxiety in the individual; and wherein the adjusting, based on the relationship, the at least one stimulus promotes the ability of the individual to perform the anxiety provoking activity by reducing stress levels of the individual with the anxiety disorder responsive to the anxiety provoking activity.

16. A method comprising:
detecting:
i. a particular activity performed by an individual;
wherein the individual has a disease or disorder that impairs the individual's ability to perform the particular activity; and
ii. brain electrical activity of the individual associated with the particular activity;

administering at least one stimulus to modulate brain electrical activity of an individual while the individual is performing the particular activity;
wherein the at least one stimulus promotes the ability of the individual to perform the particular activity;

detecting brain electrical activity of the individual while the individual is performing the particular activity;

projecting, in real time, the detected brain electrical activity of the individual while the individual is performing the particular activity onto a denoised optimal set of wavelet packet atoms to obtain a particular set of projections of the individual;

assessing, in real time, the brain electrical activity of the individual while the individual is performing the particular activity relative to a representative brain electrical activity of a plurality of individuals performing the particular activity by applying at least one machine learning algorithm to the particular set of projections of the individual;
wherein the at least one machine learning algorithm is trained by the plurality of individuals performing the particular activity and the brain electrical activity collected from the plurality of individuals associated with performing the particular activity;

determining a relationship between:
i. the particular activity performed by the individual,
ii. the detected brain electrical activity of the individual associated with the particular activity,
iii. the assessing, in real time, of the brain electrical activity of the individual associated with the particular activity relative to the representative brain electrical activity of the plurality of individuals performing the particular activity by using the at least one machine learning algorithm, and
iv. the at least one stimulus; and adjusting, based on the relationship, the at least one stimulus to promote the ability of the individual to perform the particular activity, thereby reducing at least one symptom of the disease or disorder.

17. The method of claim 16, wherein impairment of an individual's ability to perform the particular activity is a symptom characteristic of the disease or disorder.

18. The method of claim 16, wherein the administering the at least one stimulus is performed by at least one apparatus, wherein the at least one apparatus is an invasive deep brain stimulation device or a non-invasive brain stimulator.

19. The method of claim 16, wherein promoting the ability of the individual to perform the activity comprises enhancing the ability of the individual to perform the activity to at least partially achieve that of a pre-determined level of ability with respect to the particular activity.

20. The method of claim 16, wherein the disease or disorder comprises at least one of Parkinson's disease, tremors, motor dysfunction, dyskinesia, gate freeze, epilepsy, migraine headaches, pain, anxiety, depression, mood swings, attention deficit disorders, sleep disorders, or cognitive decline disorders.

* * * * *